US011779614B2

(12) United States Patent
Bogicevic et al.

(10) Patent No.: US 11,779,614 B2
(45) Date of Patent: Oct. 10, 2023

(54) PROBIOTIC BACTERIA PRECONDITIONED IN A GOS-CONTAINING MEDIUM AND USE THEREOF

(71) Applicant: SOCIETE DES PRODUITS NESTLE S.A., Vevey (CH)

(72) Inventors: Biljana Bogicevic, Bern (CH); Jeroen Andre Muller, Singapore (SG); Nicolas Page, Lausanne (CH); Guenolee Eliane Marie Prioult, Bern (CH); Wilbert Sybesma, Munsingen (CH); Thomas Sasse, Bern (CH); Benoit Marsaux, Nantes (FR)

(73) Assignee: Societe des Produits Nestle S.A., Vevey (CH)

( * ) Notice: Subject to any disclaimer, the term of this patent is extended or adjusted under 35 U.S.C. 154(b) by 23 days.

(21) Appl. No.: 16/635,667

(22) PCT Filed: Aug. 6, 2018

(86) PCT No.: PCT/EP2018/071301
§ 371 (c)(1),
(2) Date: Jan. 31, 2020

(87) PCT Pub. No.: WO2019/025637
PCT Pub. Date: Feb. 7, 2019

(65) Prior Publication Data
US 2021/0121507 A1   Apr. 29, 2021

(30) Foreign Application Priority Data

Aug. 4, 2017 (EP) ..................................... 17185017
Nov. 16, 2017 (EP) ..................................... 17202142

(51) Int. Cl.
| | | |
|---|---|---|
| *A61K 35/745* | (2015.01) | |
| *A23L 33/135* | (2016.01) | |
| *A23L 33/21* | (2016.01) | |
| *A23L 33/00* | (2016.01) | |
| *C12N 1/20* | (2006.01) | |
| *A61K 35/747* | (2015.01) | |
| *A61P 1/00* | (2006.01) | |
| *A61K 35/00* | (2006.01) | |

(52) U.S. Cl.
CPC .......... *A61K 35/745* (2013.01); *A23L 33/135* (2016.08); *A23L 33/21* (2016.08); *A23L 33/40* (2016.08); *A61K 35/747* (2013.01); *A61P 1/00* (2018.01); *C12N 1/20* (2013.01); *A23V 2002/00* (2013.01); *A23Y 2220/43* (2013.01); *A23Y 2300/21* (2013.01); *A23Y 2300/29* (2013.01); *A23Y 2300/49* (2013.01); *A23Y 2300/55* (2013.01); *A61K 2035/115* (2013.01); *C12N 2500/30* (2013.01); *C12N 2500/34* (2013.01)

(58) Field of Classification Search
None
See application file for complete search history.

(56) References Cited

U.S. PATENT DOCUMENTS

| | | | | |
|---|---|---|---|---|
| 2010/0086527 A1* | 4/2010 | Huber-Haag | ............. | A61P 1/12 424/93.45 |
| 2014/0037785 A1* | 2/2014 | Barboza | .................. | A61P 35/00 426/2 |
| 2014/0286908 A1* | 9/2014 | Garcia-Rodenas | ......................... | A61K 35/745 424/93.4 |
| 2015/0118297 A1 | 4/2015 | Ritter et al. | | |

FOREIGN PATENT DOCUMENTS

| | | |
|---|---|---|
| CN | 1777671 A | 5/2006 |
| WO | WO-2009144137 A1 * 12/2009 | ............. A23L 33/40 |
| WO | 2016071692 A1 | 5/2016 |
| WO | 2016118730 | 7/2016 |

OTHER PUBLICATIONS

Shin, HS; et al; "Growth and Viability of Commercial *Bifidobacterium* spp in Skim Milk Containing Oligosaccharides and Inulin" Journal of Food Science, 65, 884-887, 2000 (Year: 2000).*
Motherway, Mary; et al; "Metabolism of a plant derived galactose-containing polysaccharide by Bifidobacterium breve UCC2003" Microbial Biotechnology, 4, 403-416, 2010 (Year: 2010).*
69966 MRS Broth Product Data Sheet; Sigma-Aldrich/Millipore (Year: 2018).*
Simeoni, Umberto; et al; "Gut microbiota analysis reveals a marked shift to bifidobacteria by a starter infant formula containing a synbiotic of bovine milk-derived oligosaccharides and *Bifidobacterium animali* ssubsp .lactis CNCM I-3446" Environmental Microbiology, 18, 2185-2195, 2016 (Year: 2016).*
Laxmi, MP; et al; "Effect of nitrogen sources on production of [beta]-galactosidase from Bifidobacterium animalis Bb12 and *Lactobacillus delbrueckii* ssp. bulgaricus ATCC 11842 grown in whey under different culture conditions" International Food Research Journal, 18, 445-450, 2011 (Year: 2011).*
Locasrio et al. "The role of human milk oligosaccharides (HMOs) in the establishment and proliferation of Bifidobacterium infantis in the infant gut" The FASEB Journal, 2008, vol. 22, 1182.4.
O'Connell Motherway et al. "Transcriptional and functional characterization of genetic elements involved in galacto-oligosaccharide utilization by Bifidobaterium breve UCC2003" Microbial Biotechnology, 2012, vol. 6, pp. 67-79.

(Continued)

*Primary Examiner* — David W Berke-Schlessel
(74) *Attorney, Agent, or Firm* — K&L Gates LLP

(57) ABSTRACT

The present invention relates to compositions comprising galactooligosaccharides (GOS) and probiotic bacteria obtained by a process comprising the step of growing the bacteria in a medium comprising GOS, such composition having the effect of boosting the synbiotic effect of the probiotic bacteria with the GOS. Health benefits of the probiotic bacteria as obtained by such a fermentation process are also contemplated.

20 Claims, 23 Drawing Sheets

(56) References Cited

OTHER PUBLICATIONS

Andersen et al. "Transcriptional analysis of oligosaccharide utilization by Bifidobacterium lactis BI-04", BMC Genomics, 2013, vol. 14, p. 312.

Amaretti et al. "Kinetics and Metabolism of Bifidobacterium adolescentis MB 239 Growing on Glucose, Galactose, Lactose, and Galactooligosaccharides" Applied and Environmental Microbiology, Jun. 2007, vol. 73, No. 11, pp. 3637-3644.

Garrido et al. "Utilization of galactooligosaccharides by *Bifidobacterium longum* subsp. infantis isolates" Food Microbiol., Apr. 2013, vol. 33, No. 2, pp. 262-270.

Guo-Wei et al., "Effects of Stachyose, Xylooligosaccharide and Galatooligosaccharide on Growth of Bifidobacterium Bifidum", Food Science and Technology, Jun. 20, 2011, pp. 6-8.

Motherway et al., "Transcriptional and Functional Characterization of Genetic Elements Involved in Galacto-Oligosaccharide Utilization by Bifidobacterium Breve UCC2003", Microbial Biotechnology, vol. 6, Issue No. 1, Dec. 31, 2012, pp. 67-79.

Zeng, "Food Microbiological Test Technology", Jan. 31, 2016, p. 210.

Pan, "Functional Food Additives", Jan. 31, 2006, p. 91.

Yan et al., "Introduction to the Great Health Industry", May 31, 2014, pp. 197-199.

Office Action Received for Chinese Application No. 201880048397.8, dated Aug. 25, 2022, 17 Pages (6 Pages of English translation and 11 Pages of official document).

Collins et al., "Pre-treatment with Bifidobacterium breve UCC2003 modulates Citrobacter Rodentium-induced Colonic Inflammation and Organ Specificity", Microbiology, vol. 158, 2012, pp. 2826-2834.

Muller et al., "Spliceosomal Peptide P140 for Immunotherapy of Systemic Lupus Erythematosus", Results of an Early Phase II Clinical Trial, Arthritis & Rheumatism, Official Journal of the American College of Rheumatology, vol. 58, Issue No. 12, 2008, pp. 3873-3883.

De Man et al., "A Medium for the Cultivation of Lactobacilli", Journal of Applied Bacteriology, vol. 23, 1960, pp. 130-135.

Succi et al., "Pre-cultivation with Selected Prebiotics Enhances the Survival and the Stress Response of Lactobacillus rhamnosus Strains in Simulated Gastrointestinal Transit", Frontiers in Microbiology, vol. 8, Article 1067, Jun. 14, 2017, pp. 1-11.

Pregliasco et al., "A New Chance of Preventing Winter Diseases by the Administration of Synbiotic Formulations", Journal of Clinical Gastroenterology, vol. 42, Issue No. 03, Part 2, 2008, pp. S224-S233.

Russian Office Action for Appl No. 2020108088/10 dated Feb. 21, 2023.

* cited by examiner

Figure 3
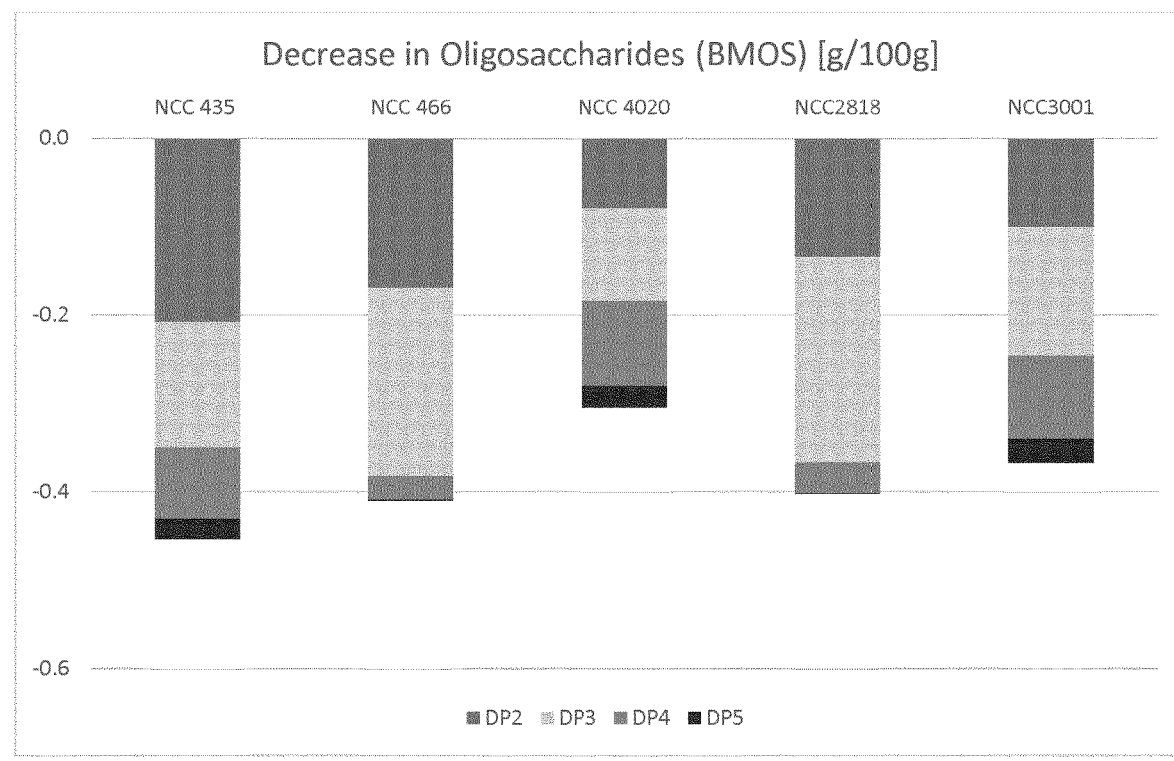
A
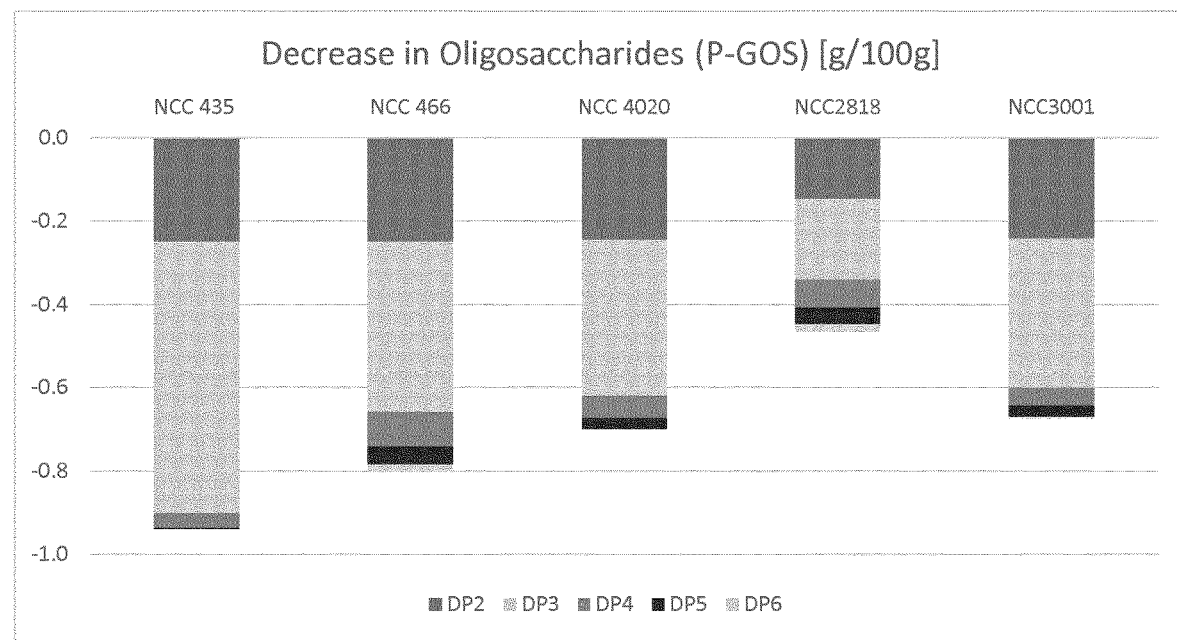
B

Figure 5
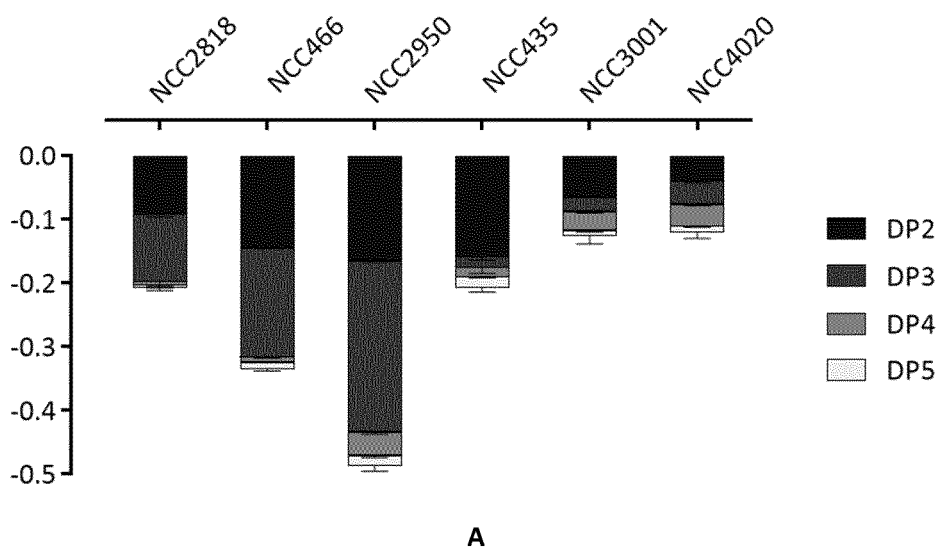
A
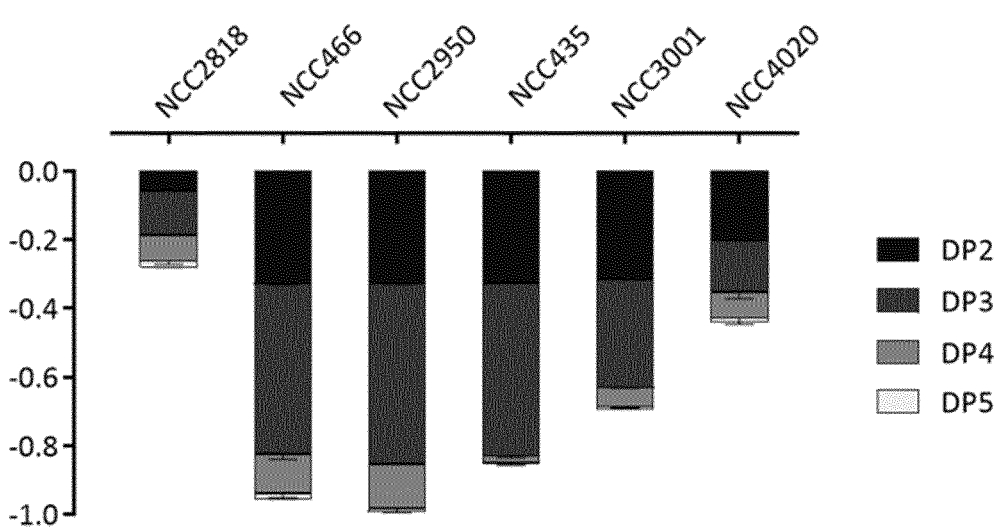
B

Figure 8
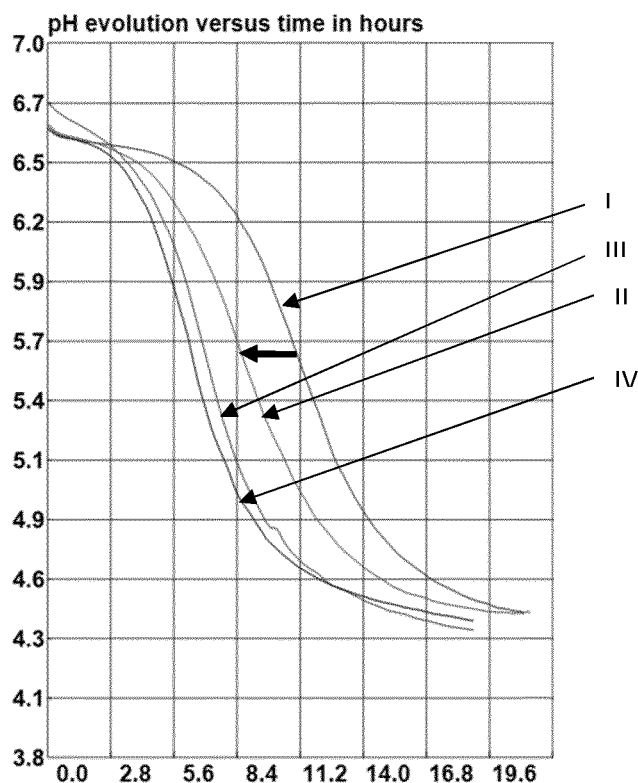
A
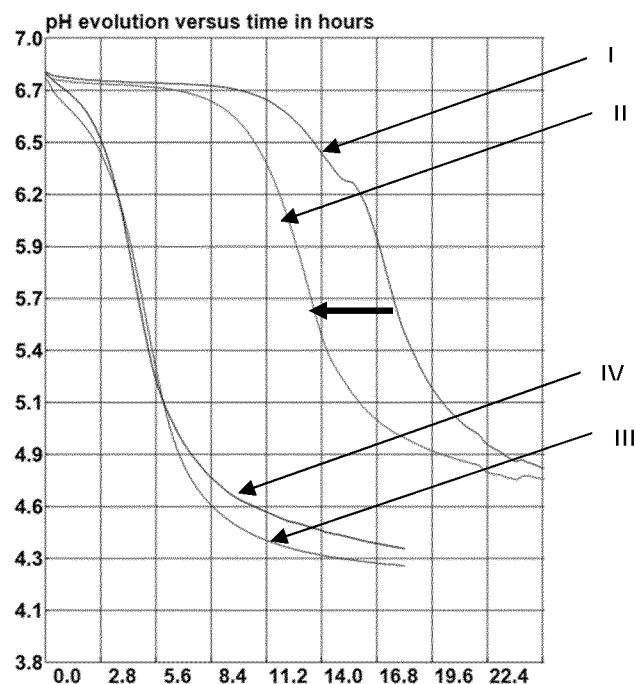
B

PROBIOTIC BACTERIA PRECONDITIONED IN A GOS-CONTAINING MEDIUM AND USE THEREOF

CROSS REFERENCE TO RELATED APPLICATIONS

The present application is a National Stage of International Application No. PCT/EP2018/071301, filed on Aug. 6, 2018, which claims priority to European Patent Application No. 17185017.5, filed on Aug. 4, 2017, and European Patent Application No. 17202142.0, filed on Nov. 16, 2017, the entire contents of which are being incorporated herein by reference.

The present invention relates to compositions comprising galacto-oligosaccharides (GOS) and probiotic bacteria obtained by a process comprising the step of growing the bacteria in a medium comprising GOS, such composition having the effect of boosting the synbiotic effect of the probiotic bacteria with the GOS. Health benefits of the probiotic bacteria as obtained by such a fermentation process are also contemplated.

BACKGROUND OF THE INVENTION

Probiotic bacteria, such as Bifidobacteria, have long been used to provide diverse health benefits, for example they have been shown as being effective in modulating the immune response, preventing and treating infections, reducing inflammation and reducing allergic response.

Bifidobacteria, in particular, are gram-positive, anaerobic rod-shaped bacteria, which are able to colonize the human gut and to hydrolyze complex carbohydrates. Members of the genus *Bifidobacterium* are frequently used as probiotic microorganisms, in a wide range of products, including infant formula.

Prebiotics have also been extensively described. Prebiotics are ingredients, such as oligosaccharides, providing health benefits when fermented by the native microflora in the intestine of a subject or by probiotic bacteria ingested simultaneously with the prebiotics. An extensive description of benefits of prebiotics can be found for example in Mcfarlane et al., *Bacterial metabolism and health-related effects of galacto-oligosaccharides and other prebiotics*, J Appl Microbiol, 2008, 104:305-344.

Combination of particular types of prebiotics and of probiotics give rise to a synergistic effect. In particular, the effect of combined prebiotic galacto-oligosaccharides (GOS) and probiotic microorganisms, such as Bifidobacteria, has been extensively documented in science articles and patents. For example combination of probiotics and GOS have been described to be beneficial for modulation of gut microbiota composition (see for example Environ. Microbiol., 2016, 18(7):2185-2195) and for modulation of immune response, such as increase of the immune defenses (see for example Br J Nutr., 2014, 111(11):1945-1956), prevention of infections (see for example Dig. Dis. Sci., 2009, 54(5):1071-8; J Clin Gastroenterology, 2008, 42(Supp 3, Part 2): 224-233) or prevention of allergy (see for example Allergy., 2011, 66(2):170-177, related to prevention of asthma-like symptoms in babies with allergic dermatitis). The effect of such synbiotics have been evidenced in particular in infants, so that several infant formula compositions comprising GOS and probiotic bacteria, for example, have been used commercially.

It has been shown that the synbiotic effect is due to the consumption of the GOS by the probiotic, e.g. Bifidobacteria, in the gastrointestinal tract of the subject. Thus further studies have been carried out with respect to the ability of probiotic bacteria to grow on and consume GOS. For example, Garrido et al., *Utilization of galactooligosaccharides by Bifidobacterium longum subsp. infantis isolates*, Food Microiol, 2013, 33(2): 262-270 studied the ability of 22 isolates of *B. longum* subsp. *infantis* to grow on GOS. All isolates showed vigorous growth on this oligosaccharides. In Vernazza et al., *Carbohydrate preference, acid tolerance and bile tolerance in five strains of Bifidobacterium*; J Appl Microbiol, 2006, 100(4):846:853, five strains of *Bifidobacterium* were analysed for their carbohydrate preference from 12 substrates. Maximum growth rates were used to compare substrate preferences. Galacto-oligosaccharides were well utilized by all the tested species. Also, in Watson et al., *Selective carbohydrate utilization by lactobacilli and bifidobacteria*; J Appl Microbiol, 2013, 114(4):1132-1146, sixty-eight bacterial strains, representing 29 human-derived lactobacilli and 39 bifidobacteria (both human- and animal-derived), were tested for their ability to metabolize 10 different carbohydrates. Galacto-oligosaccharides (GOS) and lactulose were shown to support the most favourable growth characteristics. These studies support the possibility of using synbiotics of GOS with diverse probiotic bacteria.

Other studies were focused on identifying the molecular mechanisms of GOS consumption. Namely, Motherway et al., *Transcriptional and functional characterization of genetic elements involved in galacto-oligosaccharide utilization by Bifidobacterium breve UCC2003*, Microbial Technology, 2013, 6(1): 67-79, describe the functional characterization of the *B. breve* UCC2003 gal locus which is dedicated to the utilization of galactan, a plant-derived polysaccharide comprising galactose. This study identified that the galCDEGR(A) operon was required by *B. breve* UCC2003 for the consumption of GOS.

There is a constant need to identify further synbiotic compositions. It is not only useful to identify synbiotic compositions targeting new benefits, but also to increase the efficiency of compositions already known to provide advantageous health effect. Thus it is desired to improve the efficiency of synbiotic compositions at a given dose and/or to maintain a given level of activity, while reducing the dose of probiotic bacteria and/or of prebiotics without reducing the beneficial effect of the synbiotic to the host. The present invention solves these problems.

SUMMARY OF THE INVENTION

In a first aspect, the invention provides a composition comprising an effective amount of galactooligosaccharides and a probiotic bacteria comprising the galCDEGR(A) operon, wherein said probiotic bacteria is obtained by a process comprising the steps of
  a. fermenting the probiotic bacteria in a bacterial growth medium comprising galacto-oligosaccharides and peptone; and
  b. harvesting the cultured probiotic bacteria.

In a second aspect, the invention provides a probiotic bacteria comprising the galCDEGR(A) operon obtained by a process comprising the steps of
  a. fermenting the probiotic bacteria in a bacterial growth medium comprising galacto-oligosaccharides and peptone; and
  b. harvesting the cultured probiotic bacteria;
or a composition of the invention,
for use in therapy.

In a third aspect, the invention provides a process for increasing the therapeutic effect of a composition comprising galactooligosaccharides and a probiotic bacteria comprising the galCDEGR(A) operon, comprising
  a. fermenting the probiotic bacteria in a bacterial growth medium comprising galacto-oligosaccharides and peptone; and
  b. harvesting the cultured probiotic bacteria,
before incorporating the probiotic bacteria into the synbiotic composition.

BRIEF DESCRIPTION OF THE DRAWINGS

FIG. 3: Decrease in oligosaccharides in BM+BMOS (A) and in BM+P-GOS (B) in g per 100 g medium after fermentation by the tested *Bifidobacterium* strains.

FIG. 5: Decrease in oligosaccharides in IM+BMOS (A) and in IM+P-GOS (B) in g per 100 g medium after fermentation with 5 *Bifidobacterium* strains.

FIG. 8: pH curves monitored by Cinac for one of the preconditioning experiments of *B. animalis* ssp. *lactis* strain NCC2818 on BMOS as GOS source (A) and on P-GOS as GOS source (B): (III) biomass production on dextrose, (IV) biomass production on GOS source, (I) biomass grown on dextrose upon exposure to GOS source, (II) biomass grown on GOS source upon re-exposure to GOS source. Shift in acidification during re-exposure to GOS source is indicated by the bold horizontal arrow.

DETAILED DESCRIPTION OF THE INVENTION

Figure 1:
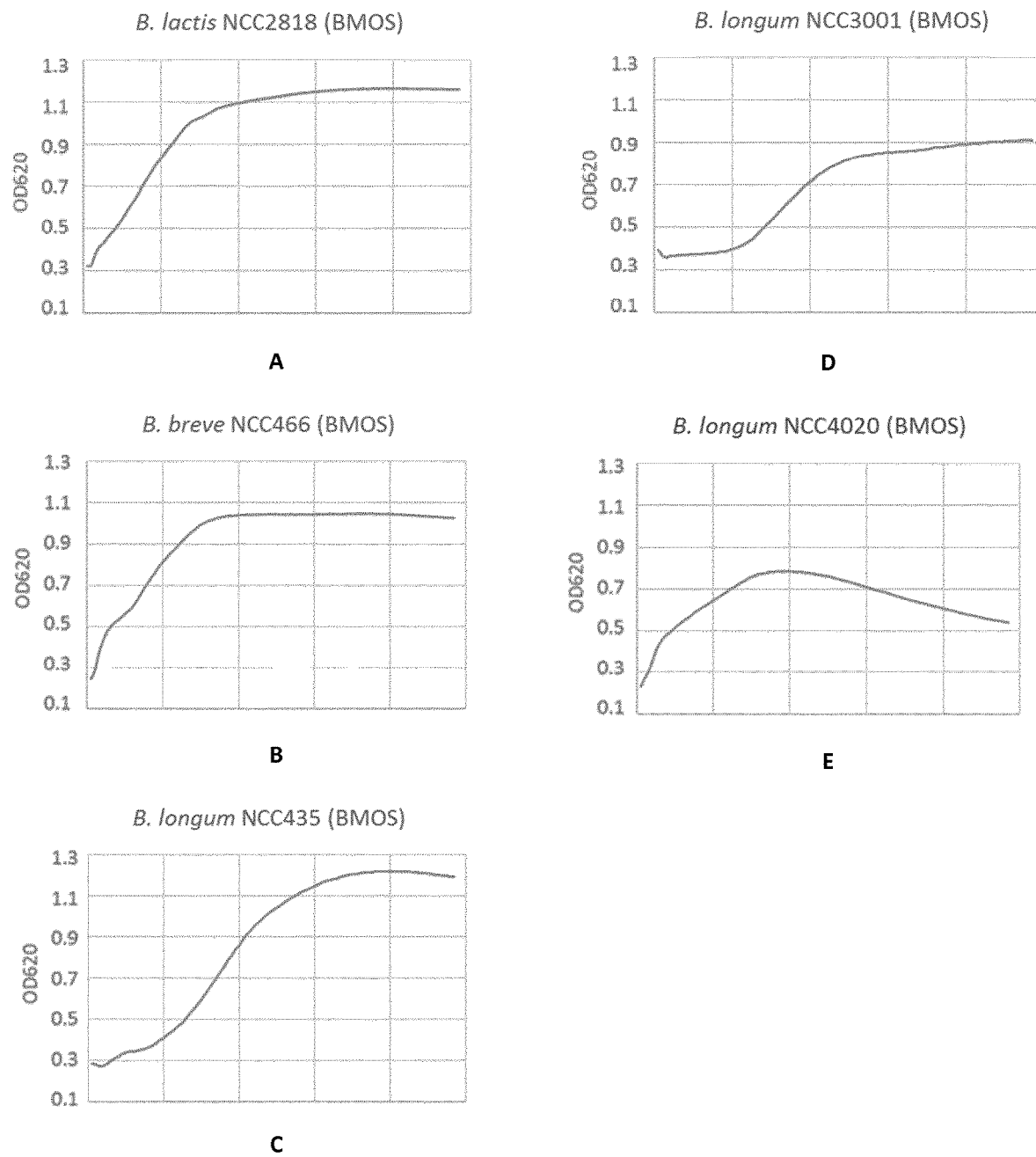
FIG. 1: Average OD curves for the tested *Bifidobacterium* strains grown overnight on BMOS: *B. animalis* ssp. *lactis* NCC2818 (A), *B. breve* NCC466 (B), *B. longum* NCC435 (C), *B. longum* NCC3001 (D) and *B. longum* NCC4020 (E).

The present invention provides synbiotic compositions having improved therapeutic effect. As will be evident from the present examples, synbiotic compositions comprising probiotic bacteria comprising the galCDEGR(A) operon and GOS have an improved effect, when the probiotic bacteria has been obtained by a process comprising the step of fermenting the probiotic bacteria in a bacterial growth medium comprising galacto-oligosaccharides and peptone.

Prior art methods for producing probiotic bacteria for industrial use involve a step of fermenting the bacteria in a growth medium comprising a sugar, such as for example glucose, fructose, sucrose, lactose or dextrose. Also the growth of probiotic bacteria on GOS has been assessed in previous studies. However none of these studies has described re-exposure of the bacteria to GOS after the end of the fermentation on GOS and none of these studies have even envisaged that probiotic bacteria grown on GOS could exhibit advantageous properties. Now the present inventors have identified that upon re-exposure of the probiotic bacteria to GOS, bacteria previously propagated on GOS showed a shorter lag phase compared to those grown on a sugar, such as dextrose. When a probiotic bacteria has been preconditioned with GOS, (i.e. it has been grown on GOS during its production process), such probiotic bacteria is then able to more rapidly start consuming GOS when it is exposed to this oligosaccharide in the gastrointestinal tract of a subject. Such faster consumption of GOS is associated with increased beneficial effect to a subject consuming the pre-conditioned bacteria and GOS and in particular an increased synbiotic effect.

As can be seen from the examples of the present application, the tested strains preconditioned with GOS showed a shorter lag phase compared to those grown on dextrose. The difference between the duration of the lag phase of the preconditioned bacteria and the non-preconditioned bacteria varies from one strain to another, but all tested strains exhibited a significantly reduced lag phase. The reduced lag phase is associated with a faster uptake of the GOS by the preconditioned bacteria and with an increased synbiotic effect. The preconditioned bacteria have namely been identified as having an improved effect to promote healthy microbiota in the gut of a subject, and to exhibit other advantages associated with a healthier microbiota, such as modulating the immune defenses of a subject, boosting the immune defenses of a subject, preventing, treating or reducing infections in a subject, preventing, treating or reducing inflammation in a subject, increasing the production of total short chain fatty acids, of acetate and/or of lactic acid in the gastrointestinal tract of a subject or for reducing the production of ammonium in the gastrointestinal tract of a subject.

Definitions

As used herein, the following terms have the following meanings.

The term "infant" means a child under the age of 12 months.

The expression "young child" means a child aged between one and three years, also called toddler.

The expression "nutritional composition" means a composition which nourishes a subject. This nutritional composition is usually to be taken orally or intravenously, and it usually includes a lipid or fat source and a protein source.

In a particular embodiment the composition of the present invention is a hypoallergenic nutritional composition. The expression "hypoallergenic nutritional composition" means a nutritional composition which is unlikely to cause allergic reactions.

In a particular embodiment the composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The term "fortifier" refers to liquid or solid nutritional compositions suitable for mixing with breast milk or infant formula.

The expressions "days/weeks/months/years of life" and "days/weeks/months/years of birth" can be used interchangeably.

The "mother's milk" should be understood as the breast milk or the colostrum of the mother.

An "oligosaccharide" is a saccharide polymer containing a small number (typically three to ten) of simple sugars (monosaccharides).

The term galacto-oligosaccharide(s) or "GOS" refers to oligosaccharide(s) comprising at least three galactose units.

The term "prebiotic" means a substrate that is selectively utilized by host microorganisms conferring a health benefit' (Expert consensus document: The International Scientific Association for Probiotics and Prebiotics (ISAPP) consensus statement on the definition and scope of prebiotics, Nature Reviews Gastroenterology & Hepatology, 2017, 14, 491-502).

The term "probiotic" means live microorganisms that, when administered in adequate amounts, confer a health benefit on the host (FAO/WHO, 2002). The microbial cells are generally bacteria or yeasts.

The term "synbiotic" means nutritional compositions or food supplements combining both probiotic(s) and prebiotic(s) and in which the prebiotic(s) selectively favours the probiotic(s) (see DeVrese and Schrezenmeir, *Probiotics, prebiotics and synbiotics in food biotechnology*, Springer Berlin Heidelberg, pp 1-66. The term "synbiotic effect" refers herein to the increase of the advantageous health effect of the synbiotic compared to the effect of the probiotic alone.

The term "cfu" should be understood as colony-forming unit.

The term 'afu' should be understood as active fluorescence unit

The term "preconditioning" the probiotic bacteria means growing the probiotic bacteria on GOS during the process of producing the probiotic bacteria. The terms "preconditioned probiotic bacteria" refer to a probiotic bacteria produced by a process including a preconditioning step.

"galCDEGR(A) operon" refers to the operon wherein all of the genes galC, galD, galE, galG and galR are present and wherein galA is optionally present. Therefore a probiotic bacteria wherein the gene galA is missing shall be understood as having the galCDEGR(A) operon.

The term "lag phase" refers to the time for the bacteria to reach the maximum of acidification rate (TM).

The term "peptone" means an autolysate or hydrolysate from a source of protein, such as yeast, meat, casein, gelatin or vegetable source. A "yeast peptone" is an autolysate or hydrolysate from yeast.

All percentages are by weight unless otherwise stated.

Preconditioned Probiotic Bacteria

The probiotic bacteria in the composition of the invention possesses the galCDEGR(A) operon. Such genes have been identified previously as being essential for probiotic bacteria, such as *Bifidobacterium breve*, to grow on GOS. See for example Motherway et al., *Transcriptional and functional characterization of genetic elements involved in galacto-oligosaccharide utilization by Bifidobacterium breve UCC*2003, Microbial Technology, 2013, 6(1): 67-79.

The galCDEGR(A) operon is a gene cluster comprising the genes galC, galD, galE, galG and galR and optionally comprising the gene galA. The genes galC, galD and galE encode an ABC transport system which is specifically internalizing GOS with low degree of polymerization (DP). These are then hydrolyzed by intracellular β-galactosidases, one of them being encoded by galG. The thereby generated glucose is directly fed into the bifid shunt whereas galactose is first converted to glucose through the Leloir pathway before feeding into the bifid shunt as well. galR is a LacI-type DNA-binding protein which controls transcription of the galCDEGR operon as well as the galA gene. galA encodes an extracellular endogalactanase degrading GOS components with a DP higher than 3 prior to internalization. galA is not necessary for probiotic bacteria to be able to consume GOS as the other genes of the operon are sufficient to consume oligosaccharides with a DP of 2 to 3, which are abundant in GOS. The following examples will show the bacterial strains with and without galA exhibit advantageously improved synbiotic properties. In an embodiment the probiotic bacteria has the galCDEGR(A) operon and the gene galA is present in the bacterial genome.

The exact sequence of the galCDEGR(A) operon slightly varies from one strain to another. However, the sequences of these sequences are sufficiently similar one to another, so that the skilled person can readily identify if one particular strain for which the genome has been sequenced possesses the galCDEGR(A) operon. The probiotic bacteria genome can be screened for sequence homology with the sequences of the galCDEGR(A) operon described in Motherway et al., *Transcriptional and functional characterization of genetic elements involved in galacto-oligosaccharide utilization by Bifidobacterium breve UCC*2003, Microbial Technology, 2013, 6(1): 67-79. The teaching of this document is hereby included by reference. Such screening can for example be performed with BLAST® (Basic Local Alignment Search Tool) provided by the US National Center for Biotechnology Information (NCBI).

Preferably the probiotic bacteria comprising galCDEGR (A) operon is a *Bifidobacterium* or a *Lactobacillus*, more preferably it is selected from *Bifidobacterium animalis* ssp. *lactis*, *Bifidobacterium longum*, *Bifidobacterium breve* and *Lactobacillus johnsonii*. Most preferably, it is selected from *Bifidobacterium animalis* ssp. *lactis* CNCM I-3446, *Bifidobacterium longum* ATCC BAA-999, *Bifidobacterium longum* ATCC 15707, *Bifidobacterium longum* CNCM I-5259, *Bifidobacterium breve* CNCM I-3914 and *Lactobacillus johnsonii* CNCM I-1225. In another preferred embodiment, the probiotic bacteria comprising galCDEGR(A) operon is a *Bifidobacterium*, more preferably it is selected from *Bifidobacterium animalis* ssp. *lactis*, *Bifidobacterium longum* and *Bifidobacterium breve*. Most preferably, it is selected from *Bifidobacterium animalis* ssp. *lactis* CNCM I-3446, *Bifidobacterium longum* ATCC BAA-999, *Bifidobacterium longum* ATCC 15707, *Bifidobacterium longum* CNCM I-5259 and *Bifidobacterium breve* CNCM 1-3914.

The probiotic bacteria present in the composition of the present invention must be live probiotic bacteria, as the synbiotic effect is associated with consumption of the GOS by the bacteria in the gastrointestinal tract of an individual consuming the composition. Bacteria are considered as "live" when they are able to multiply under controlled culture conditions and form colonies or suspensions or when the microorganism metabolic activity and/or membrane integrity can be established using methods known to the person skilled in the art, such as for example flow cytometry.

As already explained above, the probiotic bacteria to be included in the composition of the invention has to be preconditioned for it to have an improved synbiotic effect when later consumed with GOS, i.e. it must have been grown on GOS during its production process. Preferably, the probiotic bacteria has been obtained by a process comprising a step of fermenting the probiotic bacteria in a medium comprising a source of GOS and more preferably, the source of GOS is the sole source of carbohydrates. More preferably, the probiotic bacteria are obtained by a process comprising as single fermentation step, the step of fermenting the bacteria in a medium comprising a GOS source.

The GOS source used to grow the probiotic bacteria can be provided in the form of essentially pure GOS or as part of a mixture, such as a mixture of carbohydrates, comprising GOS. The essential aspect is that a sufficient amount of GOS is provided in the growth medium. In a preferred embodiment, the source of GOS is added in an amount such as providing at least 0.2%, preferably at least 0.25%, more preferably at least 0.6% of GOS in the fermentation medium. In a preferred embodiment, the source of GOS is provided in an amount such as providing at most 3%, preferably at most 2.8% of GOS in the growth medium.

When a mixture of carbohydrate is used as a source of GOS, it is preferred that the amount of GOS in such mixture is of at least 20%, preferably at least 30%, more preferably at least 40%, even more preferably at least 45%, most preferably at least 48%. Although it is not necessary that the bacteria consumes only GOS as carbon source during the fermentation, high proportion of GOS in the GOS source favours the consumption of GOS by the bacteria during fermentation over consumption of other carbohydrates, leading to improved preconditioning effect.

One particular type of mixture of carbohydrates that can advantageously be used as a source of GOS to grow the probiotic bacteria is a mixture of GOS and of cow's milk oligosaccharides. In particular mixtures of GOS with 3'-sialyllactose and/or 6'-sialyllactose are preferably used. Indeed, such mixtures contain some oligosaccharides similar to human milk, which is particularly advantageous when the composition of the invention is used as an infant formula or as a nutritional supplement for infants. Such advantageous effects are described for example in Simeoni et al.; "*Gut microbiota analysis reveals a marked shift to bifidobacteria by a starter infant formula containing a synbiotic of bovine milk-derived oligosaccharides and Bifidobacterium animalis subsp lactis CNCM I-3446*"; Environ Microbiol, 2016, 18(7): 2185-2195. Such compositions can typically be obtained from concentrating demineralized whey permeate to obtain a concentrated bovine milk oligosaccharide composition and either adding GOS or generating the GOS in situ from hydrolysis of lactose by the action of a β-galactosidase harbouring both hydrolysis and polymerase activities. The latter is preferred, as formation of GOS from hydrolysis of lactose by β-galactosidase also reduces the lactose content of the final ingredient to be used as a GOS source.

It is further preferred that the GOS source in the growth medium used to produce the probiotic bacteria is the same as the GOS ingredient that is combined with the probiotic bacteria in the composition of the present invention.

Besides the GOS source, the other components of the medium are those commonly used in the art in growth media for probiotic bacteria media containing the minimum nutritional requirements like, nitrogen source (peptone) and minerals. For example media such as MRS-type media can be used. Thus, one example of a suitable growth medium is a MRS-type medium which is modified so that a GOS source, as described above, is used as sole source of carbohydrate.

For the probiotic bacteria to exhibit the improved synbiotic effect derived from the preconditioning step described herein, the growth medium in which the probiotic bacteria is grown has to contain at least one peptone as nitrogen source. Any peptone commonly used in MRS-type media can be used, such as yeast peptone, meat peptone and casein peptone. The preferred peptone to be used varies from one strain to another. The person skilled in the art of growing a particular strain knows well which types of peptones are preferred. Peptone is in particular advantageous for strains that are sensitive to drying process, in particular to drying processes involving the use of heat, such as spray-drying, because the use of peptone in the growth medium has proven to be efficient to make the strains more resistant during such processes. Peptone is preferably present in an amount of 0.1 to 7 wt %, based on the total weight of the growth medium.

The bacterial growth medium used for fermenting the probiotic bacteria preferably also comprises yeast extract and more preferably also at least one of polyoxyethylene-sorbitan-mono-oleate (Tween® 80), DATEM and lecithin. Lecithin is particularly advantageous because it is safe for use in products for most sensitive consumers, such as infants, including preterm infants or paediatric subjects.

In addition to the peptone, it may be useful to add further nitrogen sources, such as yeast extracts. Such yeast extracts are well known to the person skilled in the art. It is one preferred source of nitrogen for probiotic bacteria, particularly suited to grow probiotic bacteria with high yield. Any type of yeast extract commonly used in growth media for probiotic bacteria can be used. The best yeast extract may vary from strain to strain. For each strain, the specific yeast extract should be selected based on the knowledge of the person skilled in the art. Yeast extract is preferably present in an amount of up to 6 wt %, based on the total weight of the growth medium.

The bacterial growth medium may comprise further ingredients, which are well known to the person skilled in the art, such as salts. Examples of salts that can be advantageously present in the growth medium include calcium carbonate, di-ammonium hydrogen citrate, sodium acetate, $MgSO_4$, $MnSO_4$ or $Na_2HPO_4$. The choice of salt(s) to be used depends on the strain to be produced and is well-known to the person skilled in the art.

The fermentation step is carried out in a way that is well known to the person skilled in the art. Fermentation includes the steps of inoculation of sterile growth medium with a defined amount of bacteria (cfu or afu), followed by incubation under defined temperature (usually 37° C.) and pH. Suitable yields can be obtained with the fermentation medium comprising GOS as described above, without changing the fermentation conditions compared to what the person skilled in the art would use for fermentation of the same strain with a standard growth medium.

The fermentation may be carried out under anaerobic or aerobic conditions, depending on the strain to be produced. When the probiotic bacteria is of the *Bifidobacterium* genus, the fermentation is preferably carried out under anaerobic conditions. Also, the pH may be controlled or not, depending on the conditions known to be the best for a specific strain to grow. The temperature and duration of the fermentation step is variable from one strain to another and is also well-known to the person skilled in the art of probiotic bacteria fermentation.

The harvesting step, which aims at separating the bacterial cells from the growth medium, is also carried out in a way that is well known to the person skilled in the art, such as by concentrating the bacteria. The harvesting step may comprises a washing step, although it is preferred to avoid the washing step whenever possible in industrial processes, to reduce cost and promote simplicity of the process.

Optionally the probiotic bacteria are dried after being harvested. The drying step may be carried out using any known method, such as spray-drying, fluid bed drying, air convective drying, atmospheric drying, roller drying or freeze drying and more preferably spray-drying.

Optionally, the bacteria may further be admixed with protective agents and/or carriers before the drying step, as known to the person skilled in the art and as appropriate depending on the drying method to be used and the bacteria to be dried.

It can easily be identified if a probiotic bacteria comprising the galCDEGR(A) operon of unknown origin is a bacteria preconditioned such as described herein by comparing its growth on GOS and on dextrose in the presence of a specific type of peptone under otherwise identical fermentation conditions. The bacteria of the present invention will grow faster on GOS than on dextrose, whereas a normal bacteria (i.e. a bacteria not preconditioned with GOS) will grow at the same rate on GOS and on dextrose or even slower on GOS than on dextrose. The specific type of peptone is a autolysate or hydrolysate from yeast with the following composition:

AN from 1.6 to 3.2
TN from 10 to 12
AN/TN from 13 to 22

Thus in a preferred embodiment, the probiotic bacteria comprising the galCDEGR(A) operon, wherein said probiotic bacteria is obtained by a process comprising the steps of fermenting the probiotic bacteria in a bacterial growth medium comprising galacto-oligosaccharides and peptone and harvesting the cultured probiotic bacteria, is able to grow faster on GOS than on dextrose in the presence of a peptone. A detailed method for identifying if an unknown probiotic bacteria is a bacteria as described herein is provided in Example 5 below.

Composition Comprising Preconditioned Probiotic Bacteria and GOS

The present invention relates to compositions comprising an effective amount, preferably a therapeutically effective amount, of GOS and a preconditioned probiotic bacteria such as described above. It is particularly advantageous to combine GOS with a bacteria preconditioned with GOS as described above, as they together exhibit a synbiotic effect, which is stronger than the synbiotic effect of GOS with the same bacteria that has not been preconditioned.

The GOS are present in the composition in an effective amount, preferably in a therapeutically effective amount. Such effective or therapeutically effective amount varies depending on the individual consuming the composition and also depending on the beneficial effect that is sought. The skilled person knows how to dose the amount of GOS depending on the subject to be treated and on the desired therapeutic effect.

Preferably, the composition comprises at least 0.2%, preferably at least 1.5% of GOS, based on dry matter. More preferably, the composition comprises 1.5 to 8%, preferably 2 to 7.5%, more preferably 3 to 8%, more preferably 4 to 7%, even more preferably 5 to 6%, and most preferably 5.5 to 6% of GOS.

The GOS contained in the composition can be provided by any kind of source of GOS, provided that an effective amount, preferably a therapeutically effective amount of GOS as defined above is provided in the composition. Preferably the source of GOS is such as described above in the section dedicated to the GOS source used in the growth medium of the bacteria. Preferably, the GOS source present in the composition of the invention is the same GOS source as the one used in the growth medium for the fermentation of the bacteria.

The probiotic bacteria present in the composition of the invention is a preconditioned bacteria, as defined above. Preferably the probiotic bacteria is present in the composition in an amount of at least 5E+05, preferably 9E+05, more preferably 2E+06 CFU per gram of product, on a dry weight basis.

The composition of the invention can be any type of composition in which probiotic bacteria can be incorporated, such as a food product, a beverage, an animal feed product, a nutritional supplement for human or animal, a pharmaceutical composition or a cosmetic composition. The product may be solid or liquid. Preferably, the composition is in powder form, in which case it can be intended to be used by the final consumer in solid (such as powder form) or semi-solid form (such as for example in the form of a paste) or, alternatively, to be reconstituted into a liquid before use.

Food products and beverages include all products intended to be consumed orally by human beings, for the purpose of providing nutrition and/or pleasure. It can for example be a nutritional composition, such as for infants and/or young children, for a pregnant or lactating woman or a woman desiring to get pregnant, for individuals in need of a special nutrition due to an adverse health condition or for elderly people. More preferably, the nutritional composition is selected from infant formula, infant cereals, follow-up formula, growing-up milks, functional milks and milk products for pregnant and lactating women or for women desiring to get pregnant. Other examples of food and beverage products include sweet and savoury snacks, powdered drinks, cereal products and dairy products, such as milk products or yogurts. In an embodiment, the product is not a fermented product. More preferably, the product is an infant formula, a follow-on formula, a growing-up milk or a product for pregnant or lactating women. Most preferably it is an infant formula.

The product can also be in the form of an animal food product or a nutritional supplement for animals. Preferably, the animal is a mammal. Examples of animals include, cows, sheep, goats, horses, dogs, cats, rabbits, rats, mice, fish, birds and the like.

Nutritional supplements are typically present in the form of a liquid, such as a refrigerated liquid, of a powder or of a tablet or capsule. Preferably it is in the form of a powder, a tablet or a capsule. Powder supplements typically encompass supplements to be dissolved in a liquid or to be sprinkled on food or in a beverage. Such supplements are intended to provide additional nutrients and/or a health benefit to the subject consuming it, as well as other beneficial ingredients, such as beneficial microorganisms, for example probiotic bacteria. A supplement according to the present invention can be used for providing nutrients and/or a health benefit to human beings, as well as to animals, as defined above. Nutritional supplements include for example powder supplements to be added to breast milk, for example for premature or low birth weight infants. It also includes supplements for pregnant or lactating woman or for woman desiring to get pregnant.

Pharmaceutical products include powder, tablet or capsule products intended to treat or prevent an adverse medical condition in a subject in need thereof, or to promote a favourable health condition.

Cosmetic compositions are typically intended for an aesthetic effect on the body and may be for topical use or may be administered by oral route, in the form of a powder, tablet or capsule.

First Medical Use

The preconditioned probiotic bacteria, or the composition comprising preconditioned probiotic bacteria and GOS, as described above, can advantageously be used in therapy. Thus the invention also provides for such probiotic bacteria and such compositions for use in therapy.

Therapy is intended here as the curing or prevention of a disease or malfunction of the body and also covers prophylactic treatment, i.e. prevention of an adverse medical condition. Therapy is also intended here to include human and animal therapy.

As will be shown in the following examples the fact that the bacteria have been preconditioned (i.e. grown on GOS during their production process), increases the synbiotic effect of the probiotic bacteria with GOS upon re-exposure of the bacteria to GOS. This makes the preconditioned probiotic bacteria and the composition described above very useful for therapeutic purposes.

Even though the growth of probiotic bacteria on GOS has been described in the prior art, no document teaches or even suggests that such bacteria grown on GOS could advantageously be re-exposed to GOS after fermentation and even less teach or suggest that such bacteria would have superior therapeutic effect (namely superior synbiotic effect when subsequently faced with GOS), compared to bacteria grown on other carbohydrates.

The therapeutic effect is only subject to exposure of the bacteria to the GOS in contact with a subject, be it for example in the gastrointestinal tract of a subject, or on the skin of a subject. Preferably, the therapeutic effect is subject to exposure of the bacteria to the GOS in the gastrointestinal tract of a subject.

In an embodiment, the present invention provides for a probiotic bacteria comprising the galCDEGR(A) operon, wherein said probiotic bacteria is obtained by a process comprising the steps of
  a. fermenting the probiotic bacteria in a bacterial growth medium comprising galacto-oligosaccharides and peptone; and
  b. harvesting the cultured probiotic bacteria,
for use in therapy, wherein the probiotic bacteria is exposed to GOS in or on an individual to be treated, preferably in the gastrointestinal tract of an individual to be treated.

In other words, the present invention relates to a method for treating a subject comprising administering to the subject an effective amount of a probiotic bacteria comprising the galCDEGR(A) operon, wherein said probiotic bacteria is obtained by a process comprising the steps of
  a. fermenting the probiotic bacteria in a bacterial growth medium comprising galacto-oligosaccharides and peptone; and
  b. harvesting the cultured probiotic bacteria,
and wherein the probiotic bacteria is exposed to GOS in or on an individual to be treated, preferably in the gastrointestinal tract of an individual to be treated.

Also, the invention provides a composition comprising an effective amount of galactooligosaccharides and a probiotic bacteria comprising the galCDEGR(A) operon, wherein said probiotic bacteria is obtained by a process comprising the steps of
  a. fermenting the probiotic bacteria in a bacterial growth medium comprising galacto-oligosaccharides and peptone; and
  b. harvesting the cultured probiotic bacteria,
for use in therapy.

In other words, the present invention relates to a method for treating a subject comprising administering to the subject an effective amount of a composition comprising an effective amount of galactooligosaccharides and a probiotic bacteria comprising the galCDEGR(A) operon, wherein said probiotic bacteria is obtained by a process comprising the steps of
  a. fermenting the probiotic bacteria in a bacterial growth medium comprising galacto-oligosaccharides and peptone; and
  b. harvesting the cultured probiotic bacteria.

In another embodiment the invention relates to the use of a probiotic bacteria comprising the galCDEGR(A) operon, wherein said probiotic bacteria is obtained by a process comprising the steps of
  a. fermenting the probiotic bacteria in a bacterial growth medium comprising galacto-oligosaccharides and peptone; and
  b. harvesting the cultured probiotic bacteria
for the manufacture of a medicament.
Preferably, the medicament is for administration together with GOS.

In a further embodiment, the invention relates to the use of a composition comprising an effective amount of galactooligosaccharides and a probiotic bacteria comprising the galCDEGR(A) operon, wherein said probiotic bacteria is obtained by a process comprising the steps of
  a. fermenting the probiotic bacteria in a bacterial growth medium comprising galacto-oligosaccharides and peptone; and
  b. harvesting the cultured probiotic bacteria
for the manufacture of a medicament.

Further Medical Uses

The invention provides a preconditioned probiotic bacteria or a composition as described above for use in the following specific therapeutic methods:
  b) for use in a method of modulating immune response in a subject;
  c) for use in a method of boosting the immune defenses in a subject;
  d) for use in a method of preventing, treating or reducing infections in a subject;
  e) for use in a method of preventing, treating or reducing inflammation in a subject; and
  f) for use in a method of promoting healthy microbiota in the gut of a subject.

The specific therapeutic uses listed above are all associated with the faster growth of microbiota and the more appropriate microbiota metabolism in the gastrointestinal tract.

The invention also provides a preconditioned probiotic bacteria or a composition as described above for use in the following specific therapeutic methods:
  a) for use in a method of improving the activity of the microbiota in the gastrointestinal tract of a subject, preferably the metabolic activity of the microbiota, preferably in the gastrointestinal tract of an infant or young child;
  b) for use in a method of increasing the production of total short chain fatty acids in the gastrointestinal tract of a subject;
  c) for use in a method of increasing acetate production in the gastrointestinal tract of a subject;
  d) for use in a method of increasing the lactic acid production in the gastrointestinal tract of a subject; or
  e) for use in a method of reducing the production of ammonium in the gastrointestinal tract of a subject.

In an embodiment, the present invention provides for a probiotic bacteria comprising the galCDEGR(A) operon, wherein said probiotic bacteria is obtained by a process comprising the steps of
  a. fermenting the probiotic bacteria in a bacterial growth medium comprising galacto-oligosaccharides and peptone; and
  b. harvesting the cultured probiotic bacteria, for use in
  I. a method of modulating immune response in a subject;
  II. a method of boosting the immune defenses in a subject;
  III. a method of preventing, treating or reducing infections in a subject;
  IV. a method of preventing, treating or reducing inflammation in a subject; or V. a method of promoting healthy microbiota in the gut of a subject, VI. a method of improving the activity of the microbiota in the gastrointestinal tract of a subject, preferably the metabolic activity of the microbiota, preferably in the gastrointestinal tract of an infant or young child;

VII. a method of increasing the production of total short chain fatty acids in the gastrointestinal tract of a subject;

VIII. a method of increasing acetate production in the gastrointestinal tract of a subject;

IX. a method of increasing the lactic acid production in the gastrointestinal tract of a subject; or X. a method of reducing the ammonium production in the gastrointestinal tract of a subject, wherein the probiotic bacteria is exposed to GOS in or on the subject, preferably in the gastrointestinal tract of the subject.

In other words, the present invention relates to a method for

I. modulating immune response in a subject;
II. boosting the immune defenses in a subject;
III. preventing, treating or reducing infections in a subject;
IV. preventing, treating or reducing inflammation in a subject; or
V. promoting healthy microbiota in the gut of a subject,
VI. improving the activity of the microbiota in the gastrointestinal tract of a subject, preferably the metabolic activity of the microbiota, preferably in the gastrointestinal tract of an infant or young child;
VII. increasing the production of total short chain fatty acids in the gastrointestinal tract of a subject;
VIII. increasing acetate production in the gastrointestinal tract of a subject;
IX. increasing the lactic acid production in the gastrointestinal tract of a subject; or
X. reducing the ammonium production in the gastrointestinal tract of a subject, comprising administering to the subject an effective amount of a probiotic bacteria comprising the galCDEGR(A) operon, wherein said probiotic bacteria is obtained by a process comprising the steps of
a. fermenting the probiotic bacteria in a bacterial growth medium comprising galacto-oligosaccharides and peptone; and
b. harvesting the cultured probiotic bacteria, and wherein the probiotic bacteria is exposed to GOS in or on the subject, preferably in the gastrointestinal tract of the subject.

Also the invention provides a composition comprising an effective amount of galactooligosaccharides and a probiotic bacteria comprising the galCDEGR(A) operon, wherein said probiotic bacteria is obtained by a process comprising the steps of
a. fermenting the probiotic bacteria in a bacterial growth medium comprising galacto-oligosaccharides and peptone; and
b. harvesting the cultured probiotic bacteria, for use in for use in
I. a method of modulating immune response in a subject;
II. a method of boosting the immune defenses in a subject;
III. a method of preventing, treating or reducing infections in a subject;
IV. a method of preventing, treating or reducing inflammation in a subject; or
V. a method of promoting healthy microbiota in the gut of a subject VI. a method of improving the activity of the microbiota in the gastrointestinal tract of a subject, preferably the metabolic activity of the microbiota, preferably in the gastrointestinal tract of an infant or young child;
VII. a method of increasing the production of total short chain fatty acids in the gastrointestinal tract of a subject;
VIII. a method of increasing acetate production in the gastrointestinal tract of a subject;
IX. a method of increasing the lactic acid production in the gastrointestinal tract of a subject; or
X. a method of reducing the ammonium production in the gastrointestinal tract of a subject.

In other words, the present invention relates to a method for
I. modulating immune response in a subject;
II. boosting the immune defenses in a subject;
III. preventing, treating or reducing infections in a subject;
IV. preventing, treating or reducing inflammation in a subject; or
V. promoting healthy microbiota in the gut of a subject,
VI. improving the activity of the microbiota in the gastrointestinal tract of a subject, preferably the metabolic activity of the microbiota, preferably in the gastrointestinal tract of an infant or young child;
VII. increasing the production of total short chain fatty acids in the gastrointestinal tract of a subject;
VIII. increasing acetate production in the gastrointestinal tract of a subject;
IX. increasing the lactic acid production in the gastrointestinal tract of a subject; or
X. reducing the ammonium production in the gastrointestinal tract of a subject,
comprising administering to the subject an effective amount of a composition comprising an effective amount of galactooligosaccharides and a probiotic bacteria comprising the galCDEGR(A) operon, wherein said probiotic bacteria is obtained by a process comprising the steps of
a. fermenting the probiotic bacteria in a bacterial growth medium comprising galacto-oligosaccharides and peptone; and
b. harvesting the cultured probiotic bacteria.

In another embodiment the invention relates to the use of a probiotic bacteria comprising the galCDEGR(A) operon, wherein said probiotic bacteria is obtained by a process comprising the steps of
c. fermenting the probiotic bacteria in a bacterial growth medium comprising galacto-oligosaccharides and peptone; and
d. harvesting the cultured probiotic bacteria
for the manufacture of a medicament for
I. modulating immune response in a subject;
II. boosting the immune defenses in a subject;
III. preventing, treating or reducing infections in a subject;
IV. preventing, treating or reducing inflammation in a subject; or
V. promoting healthy microbiota in the gut of a subject
VI. improving the activity of the microbiota in the gastrointestinal tract of a subject, preferably the metabolic activity of the microbiota, preferably in the gastrointestinal tract of an infant or young child;
VII. increasing the production of total short chain fatty acids in the gastrointestinal tract of a subject;
VIII. increasing acetate production in the gastrointestinal tract of a subject;

IX. increasing the lactic acid production in the gastrointestinal tract of a subject; or
X. reducing the ammonium production in the gastrointestinal tract of a subject.

Preferably, the medicament is for administration together with GOS.

In a further embodiment, the invention relates to the use of a composition comprising an effective amount of galactooligosaccharides and a probiotic bacteria comprising the galCDEGR(A) operon, wherein said probiotic bacteria is obtained by a process comprising the steps of
c. fermenting the probiotic bacteria in a bacterial growth medium comprising galacto-oligosaccharides and peptone; and
d. harvesting the cultured probiotic bacteria
for the manufacture of a medicament for
I. modulating immune response in a subject;
II. boosting the immune defenses in a subject;
III. preventing, treating or reducing infections in a subject;
IV. preventing, treating or reducing inflammation in a subject; or
V. promoting healthy microbiota in the gut of a subject
VI. improving the activity of the microbiota in the gastrointestinal tract of a subject, preferably the metabolic activity of the microbiota, preferably in the gastrointestinal tract of an infant or young child;
VII. increasing the production of total short chain fatty acids in the gastrointestinal tract of a subject;
VIII. increasing acetate production in the gastrointestinal tract of a subject;
IX. increasing the lactic acid production in the gastrointestinal tract of a subject; or
X. reducing the ammonium production in the gastrointestinal tract of a subject.

Methods

The invention also provides a process for increasing the therapeutic effect of a composition comprising galactooligosaccharides (GOS) and a probiotic bacteria comprising the galCDEGR(A) operon, comprising
a. fermenting the probiotic bacteria in a bacterial growth medium comprising galacto-oligosaccharides and peptone; and
b. harvesting the cultured probiotic bacteria, before incorporating the probiotic bacteria into the synbiotic composition.

As already explained above, and as evidenced in the following examples the beneficiary synbiotic effect of a probiotic bacteria comprising the galCDEGR(A) operon with GOS is increased when the probiotic bacteria is grown on GOS as source of carbohydrate, compared to probiotic bacteria grown on other oligosaccharides, such as sugars.

In a preferred embodiment, the process is a process for increasing effect of the composition to modulate the immune defenses of a subject, to boost the immune defenses of a subject, to prevent, treat or reduce infections in a subject, to prevent, treat or reduce inflammation in a subject or to promote healthy microbiota in the gut of a subject.

In another embodiment, the invention provides a method for increasing the ability of a probiotic bacteria comprising the galCDEGR(A) operon to consume GOS, comprising
a. fermenting the probiotic bacteria in a bacterial growth medium comprising galacto-oligosaccharides and peptone; and
b. harvesting the cultured probiotic bacteria.

In a preferred embodiment, such method decreases the time needed for the probiotic bacteria to start consuming GOS, when the probiotic bacteria is exposed to GOS after the harvesting step, more preferably when the probiotic bacteria is contacted with GOS in the gastrointestinal tract of a subject. The subject can be human or animal, preferably, it is human, more preferably it is an infant or a young child or a pregnant or lactating mother, most preferably it is an infant.

The present invention will now be described in further details by the way of the following examples.

EXAMPLE 1

Preconditioning Effect of Selected Bifidobacteria

Selection of *Bifidobacterium* Strains by Genome Analysis

A selection of strains of *Bifidobacterium* species *animalis, breve* and *longum*, which are associated with the infant gut microbiota, were selected for the present trials and are listed in Table 1. Where the genome was available it was screened for the presence of the galCDEGR(A) operon, required by *B. breve* UCC2003 for the consumption of GOS, using WallGene 1.5 (Genostar, Montbonnot-Saint-Martin, France).

TABLE 1

Strains selected for genome analysis.

| Species | Subsp. | Strain |
|---|---|---|
| B. animalis | lactis | NCC2818 (CNCM I-3446) |
| B. breve | | NCC466 (CNCM I-3914) |
| B. longum | longum | NCC435 (ATCC 15707) |
| B. longum | | NCC3001 (ATCC BAA-999) |
| B. longum | | NCC4020 (CNCM I-5259) |

All strains screened, for which the genome was available, possess the galCDEGR(A) operon responsible for uptake and hydrolysis of GOS (Table 2). On the other hand, the galA gene encoding an endogalactanase, which degrades GOS components with degree of polymerization (DP) >5, is only present in one *B. longum* strain.

TABLE 2

Presence (✓) or absence (x) of galCDEGR(A) operon and galA gene in selected *Bifidobacterium* strains (n/a: genome sequence not available)

| Species | Subspecies | Strain | galCDEGR(A) | galA |
|---|---|---|---|---|
| B. animalis | lactis | NCC2818 | ✓ | x |
| B. breve | | NCC466 | ✓ | ✓ |
| B. longum | longum | NCC435 | ✓ | x |
| B. longum | | NCC3001 | ✓ | x |
| B. longum | | NCC4020 | ✓ | ✓ |

2 Growth of *Bifidobacterium* Strains on GOS
2.1 Bacterial Strains

For strains NCC3001 and NCC2818, internally produced frozen starter cultures were used. For the other 15 strains, lyophilized cultures were reactivated in de Man, Rogosa, Sharpe (MRS) broth (Oxoid, Hampshire, UK)+0.05% cysteine (Sigma-Aldrich, St. Louis, USA, 30120) incubated anaerobically at 37° C. Anaerobic conditions were generated in airtight boxes by sachets (Thermo Fisher Scientific, Waltham, USA) and controlled by indicator strips (BiomÃ©rieux, France). After 2 to 3 reactivation passages in MRS broth+0.05% cysteine, aliquots were prepared with culture: sterile 85% glycerol (Merck, Germany, 104094) ratio 60:40 and stored at −80° C. Upon use, frozen cultures were thawed and one overnight passage in MRS broth+0.05% cysteine was performed under an aerobiosis prior to experiments.

2.2 Growth Screening of *Bifidobacterium* Strains on GOS

The *Bifidobacterium* strains were screened for their ability to grow on two different sources of GOS. Two different sources of GOS were evaluated: a carbohydrate mixture having the composition provided in Table 3 (BMOS; origin: Nestle; 48% GOS) and Purimune™ GOS (origin: GTC Nutrition; min. 90% GOS). Growth was monitored by continuous optical density (OD) measurements. The basal growth medium (BM) used for the selection of strains was MRS-API broth+0.05% cysteine. This basal medium was modified by adding 30 g BMOS (BM+BMOS; corresponding to 14.4 g of pure GOS) or 30 g Purimune™ GOS (BM+P-GOS; corresponding to 27 g of pure GOS) per liter as carbon source. Ingredients of MRS-API broth and stock solutions used to prepare media for this and further experiments as well as preservation procedures applied are specified in Table 4. The water used for the preparation of solutions was purified with a Purelab Ultra (ELGA Labwater, High Wycombe, UK) (18.2 MΩ-cm).

Media were inoculated with 10 µL of overnight cultures in MRS broth+cysteine. Three wells containing non-inoculated medium were also included as negative control for each of the growth media. 96-well plates were placed in a Spectra-Max 340PC384 Microplate Reader (Molecular Devices, Sunnyvale, USA) and the following kinetics settings were applied: temperature 37° C., runtime 24 h, read absorbance at wavelength 620 nm, interval 15 min and automix for 5 s before and after reading. Then the arithmetic means and standard deviations were determined from the obtained values and average curves were plotted for the different strains.

Figure 2:
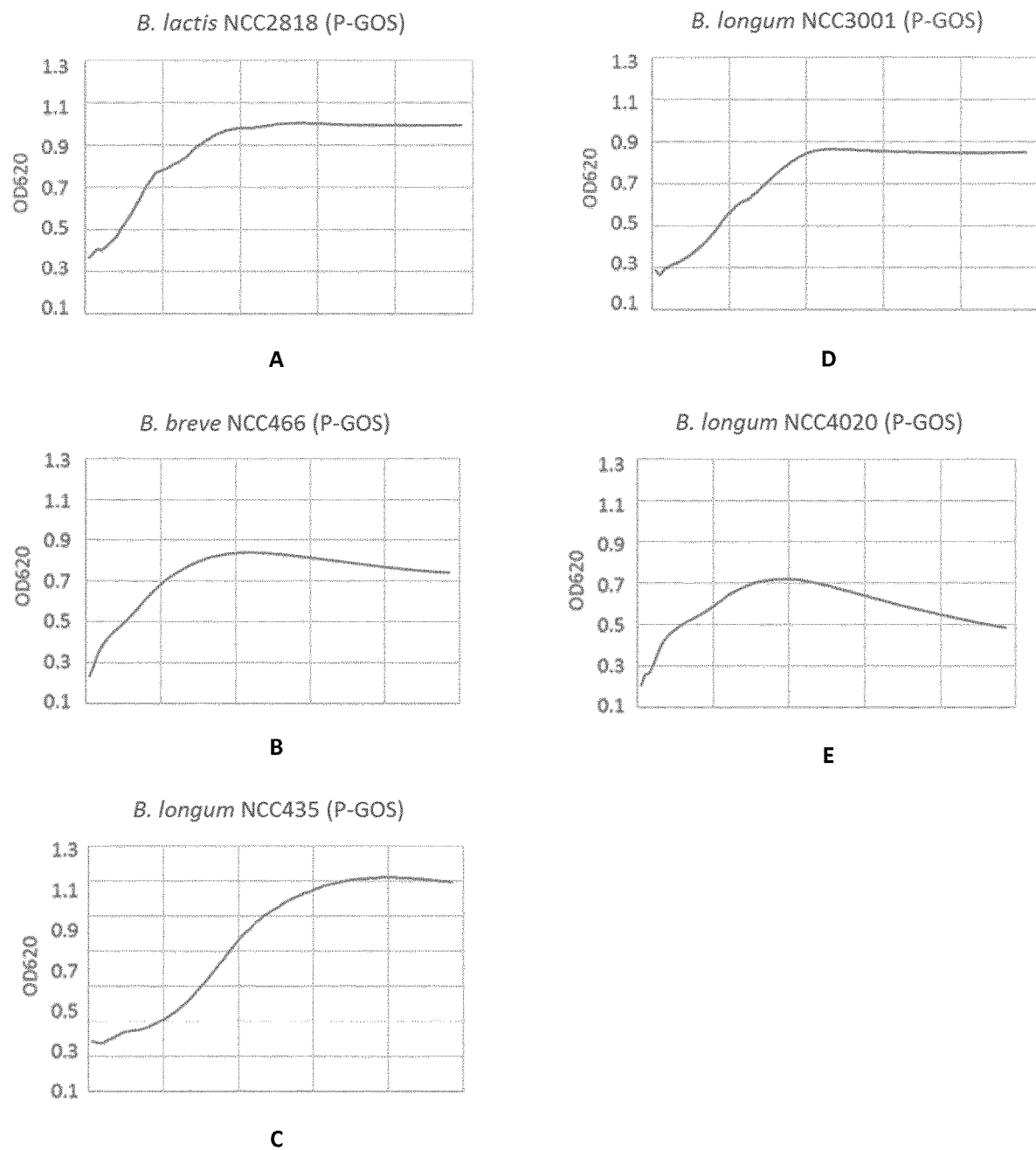
FIG. 2: Average OD curves for the tested *Bifidobacterium* strains grown overnight on P-GOS: *B. animalis* ssp. *lactis* NCC2818 (A), *B. breve* NCC466 (B), *B. longum* NCC435 (C), *B. longum* NCC3001 (D) and *B. longum* NCC4020 (E).

The average OD curves for the tested *Bifidobacterium* strains grown on BMOS and P-GOS are depicted in FIG. 1 and FIG. 2, respectively. Standard deviations of values were <0.05 (data not shown). Growth was observed for all strains on both BMOS and P-GOS. No increase in OD was observed in BM without added carbon source for any of the strains (data not shown).

TABLE 4

Ingredients, supplier and preservation method used for solutions prepared for the experiments.

| Solution | Chemicals per 1 L $H_2O$ | Supplier (Material no.) | Preservation method |
| --- | --- | --- | --- |
| MRS-API broth | 10 g Bacto Proteose Peptone No3 | Chemie Brunschwig AG, Basel, Switzerland (211677) | Autoclave (121° C., 15 min) |
| | 5 g Bacto Yeast extract | Brunschwig (212750) | |
| | 1 g Tween 80 | Brunschwig (231181) | |
| | 2 g di-ammonium hydrogen citrate | VWR International, Radnor, USA (1.01154) | |
| | 5 g sodium acetate | VWR (1.06267) | |
| | 0.1 g $MgSO_4$ | Sigma (M7506) | |
| | 0.05 g $MnSO_4$ | VWR (1.05941) | |
| | 2 g $Na_2HPO_4$ | VWR (1.06586) | |
| Cysteine | 100 g L-cysteine hydrochloride | Sigma (30120) | 0.2 µm filter (Thermo Fisher, 4500020) |
| Dextrose | 500 g dextrose monohydrat | Sugro LTD, Basel, Switzerland | 0.2 µm filter (Thermo Fisher) |
| Lactose | 400 g lactose monohydrat | Merck, Darmstadt, Germany (1.07660) | 0.2 µm filter (Thermo Fisher) |
| BMOS | 500 g BMOS | Nestlé (43061354) | Pasteurization (72° C., 15 s) |
| P-GOS | 500 g Purimune GOS | GTC Nutrition, Golden, USA (PIN 113001) | Pasteurization (72° C., 15 s) |

TABLE 3

Composition of BMOS carbohydrate mixture used as source of GOS

| Carbohydrate | Quantity (g/100 g of dry matter) |
| --- | --- |
| GOS | 48 |
| Lactose | 30 |
| Glucose | 8 |
| Galactose | 3.9 |
| 3'SL + 6'SL | >0.2 |

The growth kinetics of the *Bifidobacterium* strains were measured in triplicate in 290 µL of each growth medium (BM, BM+BMOS and BM+P-GOS) in 96-well plates.

2.3 Overnight Culture of Selected *Bifidobacterium* Strains on BMOS and P-GOS

The *Bifidobacterium* strains were tested in 20 mL growth medium (BM, BM+lactose (20 g/L lactose, Table 4), BM+BMOS, BM+P-GOS) filled in sterile 50 mL falcon tubes. BM and BM+lactose served as negative and positive growth control, respectively. Media were inoculated with 600 µL of overnight cultures in MRS broth+cysteine. In addition, 20 mL of non-inoculated media were included as negative controls. After inoculation, the tubes were incubated anaerobically at 37° C. for 20 h. After incubation, all tubes were visually screened for turbidity. For tubes containing BM+BMOS and BM+P-GOS, cell counts were determined by flow cytometry and the use of oligosaccharides was measured by high-performance liquid chromatography (HPLC).

2.4 Measuring Bacterial Growth by Flow Cytometry

Cell counts were determined by flow cytometry as described in ISO 19344:2015 (IDF 232). In a first step, serial decimal dilutions of the samples were performed in tryptone salt (Oxoid, LP0042) solution. 100 µL of the appropriate dilutions, containing an optimal value of approximately $10^6$ cfu/mL, were transferred to 880 µL of phosphate buffered saline (PBS, Sigma, P4417) in a 96 deep well plate. Subsequently, 10 µL propidium iodine (Thermo Fisher, P1304MP) 0.2 mM solution in water and 10 µL Syto 24 (Thermo Fisher, S7559) 0.1 mM solution in water were added. Then the plate was thoroughly mixed at 1500 rpm for 30 s using a MixMate (Eppendorf AG, Hamburg, Germany) before being incubated in a water bath at 37° C. for 15 min under exclusion of light. The labeled samples were measured using a Cytoflex S (Beckman Coulter Inc., Brea, USA) with the following settings: gain: FSC (120), SSC (142), Syto24 (204), PI (115); primary threshold: channel FSC, 5000 (height) and secondary threshold: channel Syto24, 11,000 (height); width: channel FSC; mix 1.5 s; backflush 6 s; flow rate: 30 µL/min; record 10,000 events in target or 300 s. In this way, active fluorescent units per mL (afu/mL) of samples were determined.

2.5 Determination of Use of Oligosaccharides by HPLC

The amount of total oligosaccharides in samples was determined using HPLC after labeling with 2-aminobenzamide (2-AB) as previously described by Austin et al., *Determination of beta-galactooligosaccharides by liquid chromatography*; International Journal of Analytical Chemistry, 2014: 10, with some modifications. Samples from overnight culture in BM+3% BMOS resp. 3% P-GOS were centrifuged at 5000 g for 10 min (Heraeus Multifuge X1R, Thermo Fisher). Supernatants were transferred to 2 mL Eppendorf tubes and heat treated at 80° C. for 15 min using a Dri-Block DB-2D (Techne Ltd., Cambridge, UK) before being stored at −18° C. Upon use samples were diluted in deionized water (18 MΩ) produced by Milli-Q system (Millipore, Billerica, USA) to obtain approximately 2 mg oligosaccharides per mL sample. To 500 µL of diluted sample solution 200 µL of laminaritriose (Sigma, L1664) solution (0.3 mmol/L) was added. The mixture was vortexed before a 20 µL aliquot was transferred to 200 µL 2-AB reagent, which was prepared by completely dissolving 0.35 mol/L 2-AB (Sigma, A89804) and 1.0 mol/L sodium cyanoborohydride (Sigma, 71435) in dimethyl sulfoxide (Sigma, 41640) containing 30% acetic acid (Merck, 1.00063) using an ultrasonic bath. This aliquot—2AB mixture was vortexed well and then incubated at 65±1° C. in a water bath for 2 h±5 min. After the reaction, tubes were mixed and cooled down by placing them at 4° C. for at least 10 min. Subsequently 1.5 mL acetonitrile (Merck, 1.00030)/water (75/25) was added. Tubes were then vortexed and centrifuged at 10,000×g for 5 min (Eppendorf 5424 Microcentrifuge) before transferring 1 mL of supernatant to a vial suitable for the HPLC autosampler.

Labeled oligosaccharides were separated using an Ultimate 3000 RS (Dionex, Sunnyville, USA) in the configuration described by Benet and Austin (2011) on TSK Gel Amide-80 guard (3.2×15 mm, 3 µm) and analytical (4.6×150 mm, 3 µm) columns (Tosoh Bioscience, Stuttgart, Germany). Detection was performed by a Dionex RF-2000 using $\lambda ex=330$ nm and $\lambda em=420$ nm. Eluents A and B were 100% acetonitrile and 50 mmol/L ammonium formate (ammonium hydroxide solution (Merck, 1.05432), formic acid (Merck, 1.00264)) at pH 4.4, respectively. A 10 µL sample of the labeled oligosaccharide solution was injected onto a guard cartridge under isocratic conditions (98% A) at a flow rate of 1 mL/min for 7.5 min. Then the eluent was directed from the guard cartridge onto the analytical column held at 23° C. and the mobile phase was put to 84% A over 0.5 min. Oligosaccharides were separated using the following conditions: 84% A from 8 to 16 min, followed by a linear gradient to 61% A at 50 min. At 51 min the column was washed for 3 min by decreasing the flow rate to 0.8 mL/min and changing the eluent composition to 20% A. Subsequently, the eluent composition was restored to 90% A over 1 before the flow rate was set to 1.0 mL/min again. These conditions were applied for 6 min under which the column re-equilibrated before returning the system to the load conditions for the subsequent sample.

Oligosaccharide concentrations were determined by integrating the peaks in the obtained fluorescence chromatograms. Peak areas (relative to the internal standard) were compared to those of a calibration curve which was obtained by measuring different concentrations of maltotriose (Sigma, M8378) with laminaritriose as internal standard. The hereby obtained molar concentration of each component was converted to a mass concentration using the molecular weight (previously assigned by mass spectrometry by Austin et al., *Determination of beta-galactooligosaccharides by liquid chromatography*; International Journal of Analytical Chemistry, 2014: 10).

Chromeleon 7.2 Chromatography Data System Software (Dionex) was used for the integration and evaluation of the chromatograms obtained. In order to determine the amount of oligosaccharides used by the different strains, the values obtained for media after fermentation were subtracted from the ones before fermentation. All measurements were performed in duplicate. For the thereby obtained values the arithmetic means as well as standard deviations were calculated.

2.6 Results

Chromatograms obtained for BM+BMOS and BM+P-GOS media before fermentation showed substantial differences in profiles. BM+BMOS contained much more lactose and hence a smaller proportion of total oligosaccharides amounting to 1.19 g compared to 1.73 g per 100 g medium for BM+P-GOS (Table 5).

TABLE 5

Amounts of oligosaccharides fractions in BM + BMOS and BM + P-GOS per 100 g medium.

| OS [g/100 g] | BM + BMOS | BM + P-GOS |
|---|---|---|
| DP2 | 0.26 | 0.27 |
| DP3 | 0.64 | 0.92 |
| DP4 | 0.23 | 0.39 |
| DP5 | 0.06 | 0.13 |
| Total | 1.19 | 1.73 |

While both GOS ingredients mostly contained small oligosaccharides with a DP of 2 to 4, P-GOS showed a higher variety of different compounds which were also present in a larger quantity. This was especially the case for DP3 and DP4 oligosaccharides. As a consequence of these distinctions between the GOS ingredients, there were as well differences in use of oligosaccharides by *Bifidobacterium* strains between BMOS and P-GOS. In addition, different *Bifidobacterium* strains showed diverse usage patterns. While NCC2818 consumed specific compounds, NCC435 showed a more general usage pattern by reducing most peaks of DP2 and DP3. Furthermore, NCC435 consumed almost all of the available lactose apart from metabolizing a lot of oligosaccharides, while NCC2818 used less lactose and less oligosaccharides.

Figure 4:
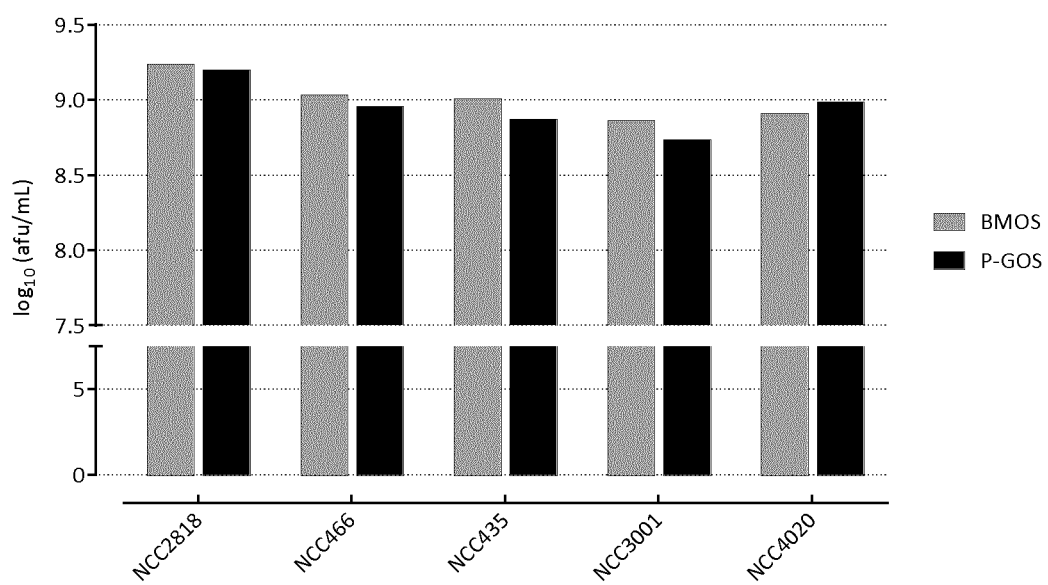
FIG. 4: Cell counts of the tested *Bifidobacterium* strains grown in BM+BMOS and BM+P-GOS determined by flow cytometry.

Analyzing the cumulative decrease in oligosaccharides during fermentation showed that all of the 5 tested *Bifidobacterium* strains consumed oligosaccharides present in BMOS and P-GOS. In BM+BMOS medium, *B. animalis* ssp. *lactis* NCC2818 and the *B. breve* strain mostly used oligosaccharides with DP2 and DP3 (FIG. 3 (A)). On the other hand, the *B. longum* strains consumed in addition to DP2 and DP3 also bigger oligosaccharides with DP 4 and 5. Moreover, the *B. longum* strain NCC4020 possessing galA did not metabolize more oligosaccharides than the strains without the gene. With BM+P-GOS, all strains except NCC2818 used over 90% of available oligosaccharides with DP2 (FIG. 3(B)). Furthermore, the strains mostly metabolized the DP3 fraction and low amounts of DP4. Some strains additionally used oligosaccharides with DP5, however, without strains of the same species showing a general pattern of consumption. On the other hand, the low consumption of oligosaccharides by *B. animalis* ssp. *lactis* NCC2818 grown on P-GOS was not in correlation with its high cell count of 9.2 $\log_{10}$ (afu/mL). The cell counts obtained for all strains lied in the same range with values of 8.8-9.2 $\log_{10}$ (afu/mL) and 8.7-9.2 $\log_{10}$ (afu/mL) observed for growth on BMOS and P-GOS, respectively (FIG. 4).

Figure 6:
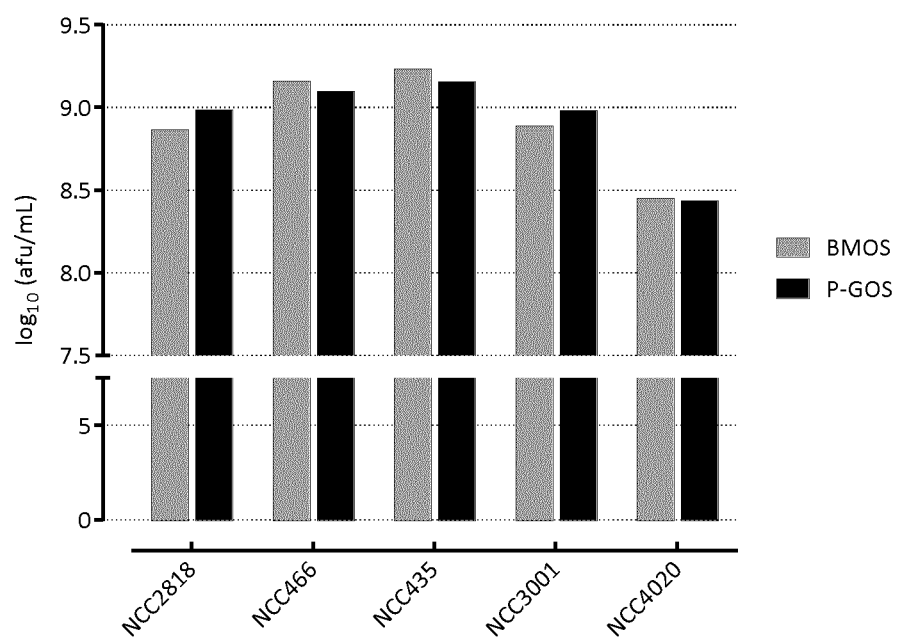
FIG. 6: Cell counts of the tested *Bifidobacterium* strains grown in IM+BMOS and IM+P-GOS determined by flow cytometry.

Since MRS-API broth is not used for fermentations at large scale and the selected strains showed good growth in industrial medium used for commercial production of *B. animalis* ssp. *lactis* NCC2818 (IM), the growth medium was changed from BM to IM for the following preconditioning experiments. In order to confirm the use of oligosaccharides in the new medium as well, the overnight culture experiment with subsequent analysis of consumption of oligosaccharides was repeated once in IM for the selected strains. In IM+BMOS, the *B. longum* strains and *B. animalis* ssp. *lactis* showed low use of oligosaccharides with total oligosaccharides consumption of 0.12 to 0.21 g per 100 g medium (FIG. 5). For the *B. breve* strain on the other hand, obtained results were similar to the ones observed in BM. In IM+P-GOS, NCC2818 and NCC4020 showed lower use of oligosaccharides as well. The remaining strains metabolized similar amounts of GOS as in BM, with the two *B. breve* strains showing slightly higher consumption. Cell counts measured lied between 8.9 and 9.2 $\log_{10}$ (afu/mL) on both carbon sources for all strains except NCC4020 which reached lower cell counts of 8.4 $\log_{10}$ (afu/mL) (FIG. 6).

3 Preconditioning Experiment

Figure 7:
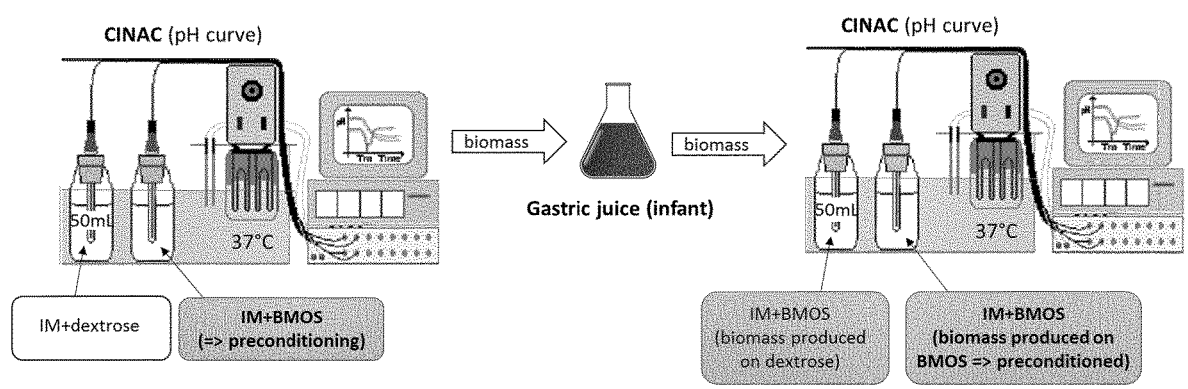
FIG. 7: Experimental setup of the preconditioning experiment with BMOS used as GOS source.

In a first step, biomass was produced during fermentation either on dextrose or a GOS ingredient (BMOS or P-GOS). It was then exposed to gastric juice before being re-exposed to the GOS ingredient during fermentation. FIG. 7 shows a scheme of the setup of the preconditioning experiment when BMOS was used as source of GOS. Similar set up also applied with P-GOS where BMOS was replaced by P-GOS in the scheme; Cinac modified from Wang; Préadaptation et cryotolérance chez *Lactobacillus acidophilus*: effet des conditions opératoires; Paris, 2005, Institut National Agronomique Paris-Grignon.

3.1 Preconditioning

The *Bifidobacterium* strains were grown in triplicate in 50 mL growth medium (IM+dextrose (30 g/L dextrose, Table 4), IM+BMOS) filled in sterile 100 mL bottles. Media were inoculated with $10^7$ (afu/mL) and incubated at 37° C. in a water bath. Cinac pH monitoring system (Ysebaert, Frepillon, France) was used for monitoring acidification during fermentation, which can be used as an indication for the growth of lactic acid producing bacteria (Spinnler and Corrieu 1989). After fermentation cell counts were determined by flow cytometry and pour plating. Furthermore, the same experiment was repeated once in IM+P-GOS for strain NCC2818, measuring cell count using flow cytometry.

3.2 Simulation of Gastric Juice

A volume containing $5 \times 10^9$ cells (determined by flow cytometry) was removed from each bottle after fermentation and transferred to sterile Eppendorf tubes. These samples were then centrifuged with a Biofuge pico (Heraeus Instruments, Hanau, Germany) at 16060×g for 5 min. Subsequently, supernatants were discarded and the pellets were resuspended in 1 mL 0.9% NaCl (Sigma, S9888) solution. This washing step was repeated another time to remove residues of the growth medium. Of the thereby obtained biomass suspension at $5 \times 10^9$ (afu/mL), 200 µL were added to 1.8 mL gastric juice in a 2 mL Eppendorf tube. Gastric juice contained per liter distilled water 2.3 g pepsin (Sigma, P7000) and 5 g NaCl (Sigma, S9888). It was adjusted to a pH of 4.5 to simulate infant conditions. Tubes with the biomass-gastric juice mixture were vortexed well and subsequently incubated in a water bath at 37° C. for 30 min. 100 µL of sample were taken from tubes before and after incubation in order to determine the loss in cell count due to gastric juice by flow cytometry as described in chapter 2.4.

3.3 Re-Exposure of Strains to GOS

Of the remaining biomass-gastric juice mixture a volume containing $5 \times 10^8$ cells was used to inoculate 50 mL of IM+BMOS or IM+P-GOS medium ($10^7$ (afu/mL)). Subsequent incubation, pH monitoring by Cinac and determination of cell count after fermentation were performed the same way as previously described.

3.4 Pour Plating

Cell counts were determined by pour plating. Briefly, serial decimal dilutions of the samples were performed in tryptone salt (Oxoid, LP0042) solution. Subsequently, 100 µL of the appropriate dilutions were transferred to petri dishes and mixed with MRS agar (AES Chemunex, Bruz, France)+0.5 g/L cysteine. Analysis was performed in duplicate. Plates were then incubated in airtight boxes under anaerobic conditions at 37° C. for 48 h. Colony forming units per mL (cfu/mL) were calculated from the number of colonies counted on plates with appropriate dilution by determining their arithmetic mean.

3.5 Results 3.5.1 *B. Animalis* ssp. *Lactis* NCC2818

During the first growth passage, the development of pH was very similar on both carbon sources, with media containing dextrose and BMOS showing end pH of 4.3 and 4.4, respectively for one of the three replicates shown as representative (FIG. 8(A)). Moreover, no differences were observed in the cell counts reached at the end of fermentation. For growth on dextrose, cell counts of 9.06±0.15 $\log_{10}$ (afu/mL) and 8.77±0.36 $\log_{10}$ (cfu/mL) were determined by flow cytometry and pour plating, respectively (Table 6). For growth on BMOS, measured cell counts amounted to 8.88±0.20 $\log_{10}$ (afu/mL) (FIG. 9) for the flow cytometry method and 8.78±0.05 $\log_{10}$ (cfu/mL) for pour plating. The subsequent treatment with gastric juice did not lead to a reduction in live cells for *B. animalis* ssp. *lactis* grown on either of the two carbon sources, with changes in $\log_{10}$ (afu/mL) of <10.051 (FIG. 10). Upon re-exposure of the biomasses to BMOS, the cells previously propagated on BMOS showed an approximately 2.5 h shorter lag phase compared to those grown on dextrose (FIG. 8(A)).

Shortening of the lag phase is key to improve the in vivo synbiotic effect, as a fast effect is needed, in particular taking into account the feeding pattern of infants, which are fed in average every three hours.

Figure 11:
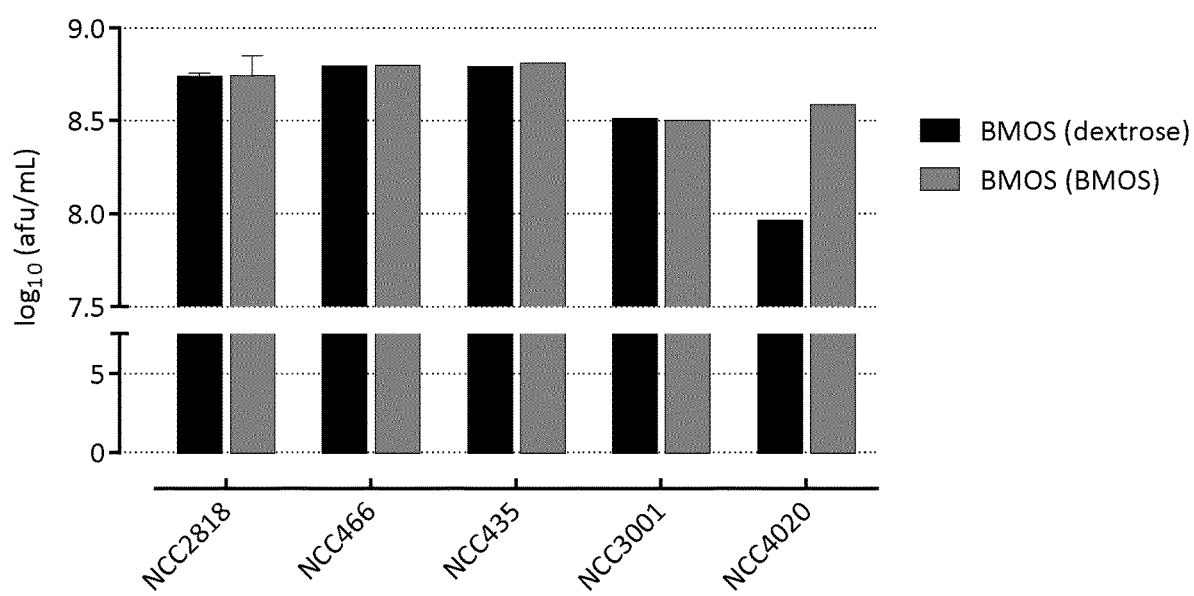
FIG. 11: Cell counts of the *Bifidobacterium* strains, either propagated on dextrose or BMOS, upon re-exposure to BMOS after being exposed to gastric juice determined by flow cytometry.

Both fermentations reached an equal final pH of approximately 4.4, which was in the same range as the ones observed during the propagation of the cells. Moreover, final cell counts of 8.74±0.02 $\log_{10}$ (afu/mL)/8.67±0.08 $\log_{10}$ (cfu/mL) and 8.73±0.12 logo (afu/mL)/8.73±0.17 $\log_{10}$ (cfu/mL) were reached for biomass previously grown on dextrose and preconditioned cells, respectively (FIG. 11).

TABLE 6

Cell counts reached by *B. animalis* ssp. *lactis* NCC2818 during fermentations of preconditioning experiment, determined by flow cytometry and pour plating.

| Fermentation | $\log_{10}$ (afu/mL) | $\log_{10}$ (cfu/mL) |
|---|---|---|
| Propagation on dextrose | 9.06 ± 0.15 | 8.77 ± 0.36 |
| Propagation on BMOS | 8.88 ± 0.20 | 8.78 ± 0.05 |
| Exposure to BMOS (biomass grown on dextrose) | 8.74 ± 0.02 | 8.67 ± 0.08 |
| Re-exposure to BMOS (biomass grown on BMOS) | 8.73 ± 0.12 | 8.73 ± 0.17 |

The experiment was repeated for strain NCC2818 with P-GOS as GOS ingredient. The final pH reached for the propagation of cells was 4.3 and 4.4 for growth on dextrose and P-GOS, respectively (FIG. 8(B)). Cell counts reached 9.16 $\log_{10}$ (afu/mL) on dextrose and 9.04 $\log_{10}$ (afu/mL) on P-GOS (Table 7). No loss in biomass was observed during exposure to gastric juice with a measured change of +0.04 $\log_{10}$ (afu/mL). Upon fermentation on P-GOS, final pH of 4.8 and cell counts of 8.9 $\log_{10}$ (afu/mL) were reached for both biomasses, preconditioned and not preconditioned one. The lag phase of preconditioned cells was approximately 3 hours shorter (FIG. 8(B)). However, at the same time it was more than 6 hours longer than in the previous fermentation in which the biomass was produced on P-GOS.

TABLE 7

Cell counts reached by *B. animalis* ssp. *lactis* NCC2818 during fermentations of preconditioning experiment with P-GOS, determined by flow cytometry.

| Fermentation | $\log_{10}$ (afu/mL) |
|---|---|
| Propagation on dextrose | 9.16 |
| Propagation on P-GOS | 9.04 |
| Exposure to P-GOS (biomass grown on dextrose) | 8.92 |
| Re-exposure to P-GOS (biomass grown on P-GOS) | 8.91 |

3.5.2 Other Strains

Figure 9:
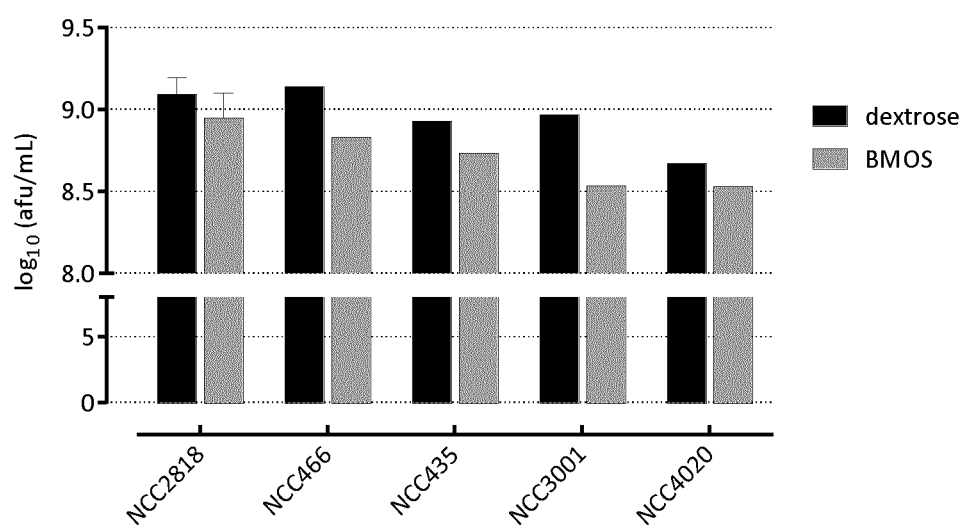
FIG. 9: Cell counts of the *Bifidobacterium* strains propagated in IM+dextrose and IM+BMOS medium determined by flow cytometry.
Figure 10:
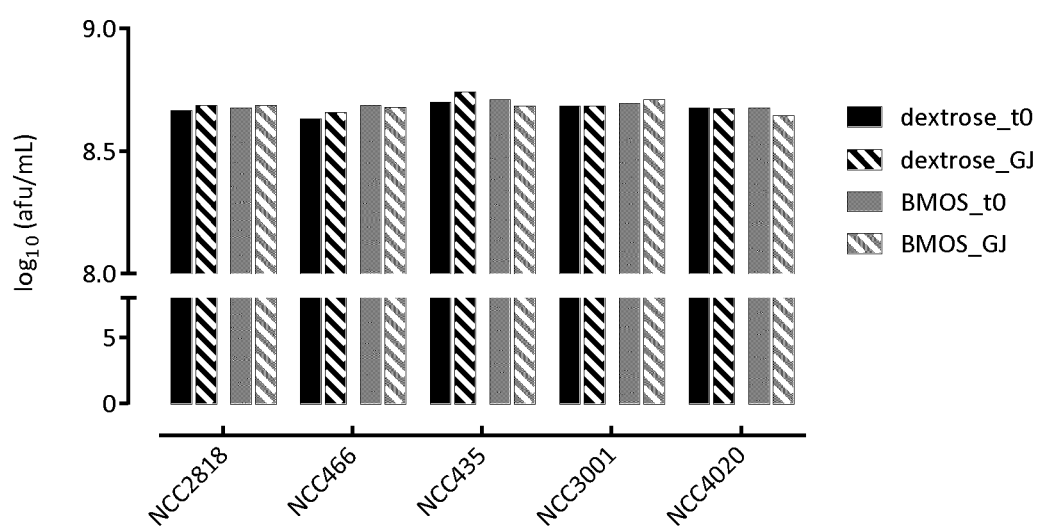
FIG. 10: Cell counts of the *Bifidobacterium* strains, propagated on either dextrose or BMOS, before (t0) and after (GJ) exposure to gastric juice determined by flow cytometry.

The other strains reached cell counts of 8.7-9.1 $\log_{10}$ (afu/mL) and 8.5-8.8 $\log_{10}$ (afu/mL) after propagation on dextrose and BMOS, respectively, showing slightly lower numbers when grown on BMOS for all strains (FIG. 9). When the obtained biomasses were exposed to gastric juice, no changes in cell counts were observed for any of the strains with changes in $\log_{10}$ (afu/mL) of <|0.05| (FIG. 10). During subsequent growth of cells on BMOS, strains NCC466, NCC2950 and NCC435 reached cell counts of 8.8 $\log_{10}$ (afu/mL) regardless of whether they were preconditioned on BMOS or not (FIG. 11). These values lied in the same range as the ones obtained for NCC2818 which grew to 8.73±0.12 $\log_{10}$ (afu/mL). Strain NCC3001 reached cell counts of 8.5 $\log_{10}$ (afu/mL) for both biomasses. On the other hand, *B. longum* NCC4020 was the only strain for which higher cell counts were measured for biomass previously grown on BMOS compared to the one propagated on dextrose, with values amounting to 8.6 $\log_{10}$ (afu/mL) and 8.0 $\log_{10}$ (afu/mL).

Figure 12:
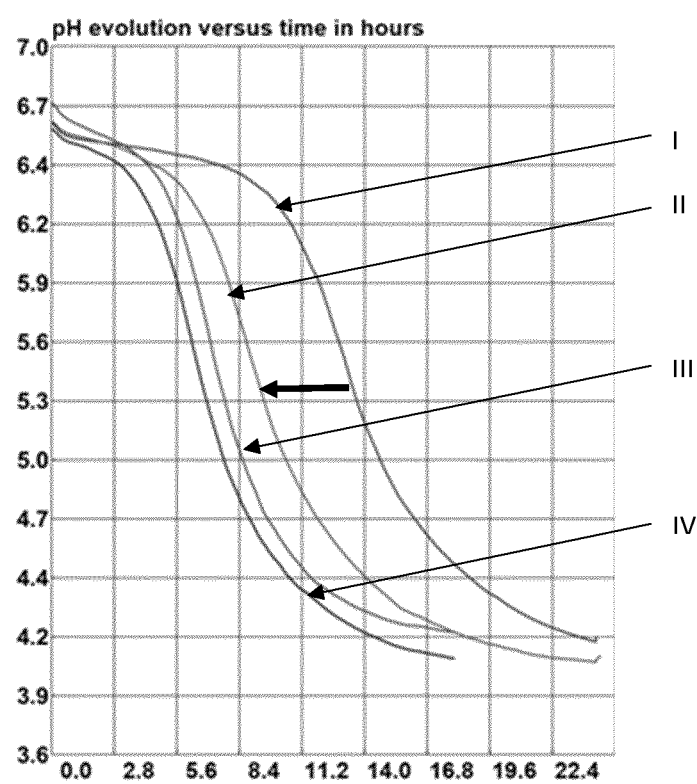
FIG. 12: pH curves monitored by Cinac for one of the preconditioning experiments of *B. breve* strain NCC466 on BMOS as GOS source: (III) biomass production on dextrose, (IV) biomass production on GOS source, (I) biomass grown on dextrose upon exposure to GOS source, (II) biomass grown on GOS source upon re-exposure to GOS source. Shift in acidification during re-exposure to GOS source is indicated by the bold horizontal arrow.

For strain NCC466, no differences were observed in acidification for the propagation on dextrose and BMOS (FIG. 12). However, upon (re-)exposure of this biomass to BMOS, the preconditioned cells showed an approximately 4 h shorter lag phase than the ones grown on dextrose.

Figure 13:
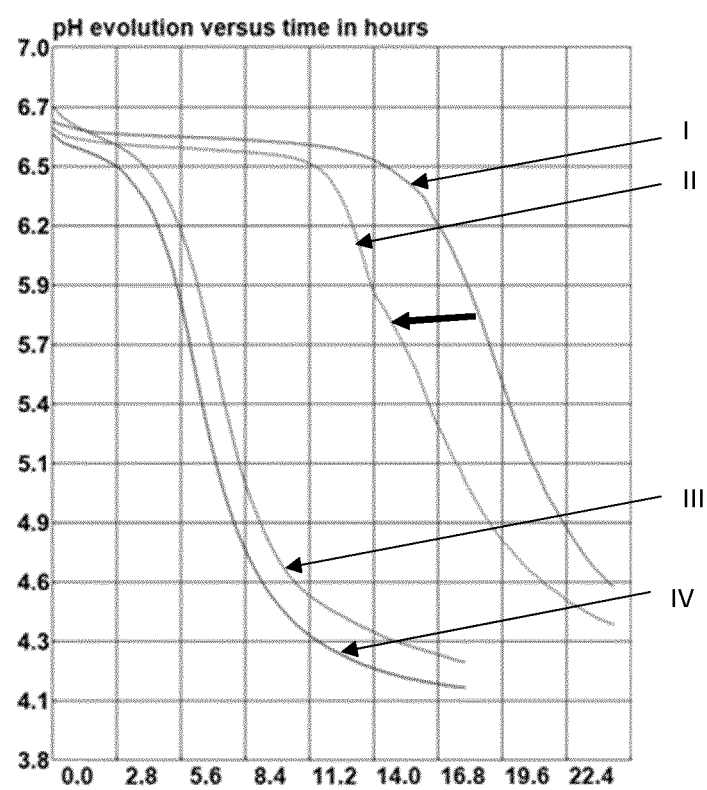
FIG. 13: pH curves monitored by Cinac for one of the preconditioning experiments of *B. longum* strain NCC435 on BMOS as GOS source: (III) biomass production on dextrose, (IV) biomass production on GOS source, (I) biomass grown on dextrose upon exposure to GOS source, (II) biomass grown on GOS source upon re-exposure to GOS source. Shift in acidification during re-exposure to GOS source is indicated by the bold horizontal arrow.
Figure 14:
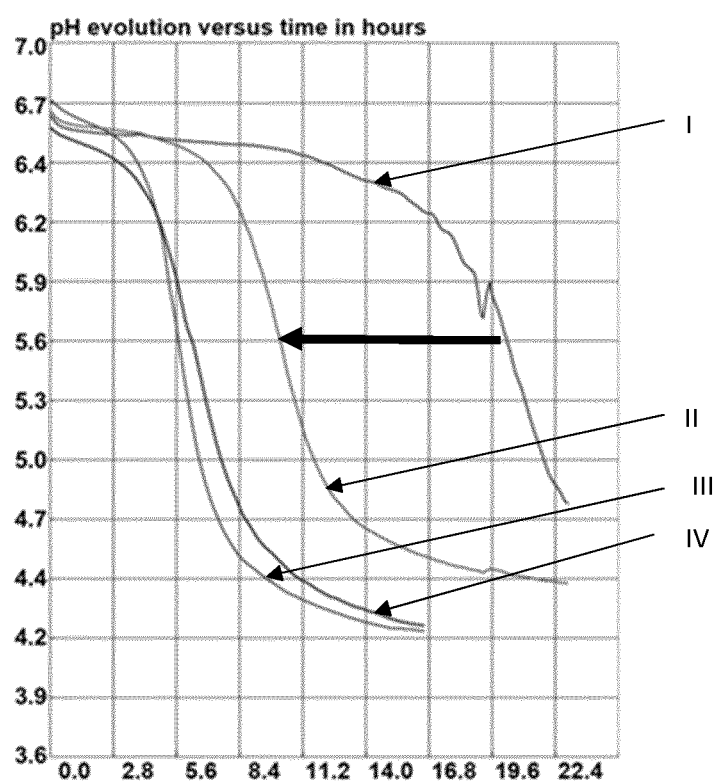
FIG. 14: pH curves monitored by Cinac for one of the preconditioning experiments of *B. longum* strain NCC3001 on BMOS as GOS source: (III) biomass production on dextrose, (IV) biomass production on GOS source, (I) biomass grown on dextrose upon exposure to GOS source, (II) biomass grown on GOS source upon re-exposure to GOS source. Shift in acidification during re-exposure to GOS source is indicated by the bold horizontal arrow.

For *B. longum* strains NCC435 and NCC3001, which do not possess the galA gene, no notable differences were observed between the growth of biomass on dextrose and BMOS. When these cells were grown on BMOS after exposure to gastric juice, the preconditioned ones showed a shorter lag phase of approximately 3 hours and more than 5 hours for strains NCC435 (FIG. 13) and NCC3001 (FIG. 14), respectively.

Figure 15:
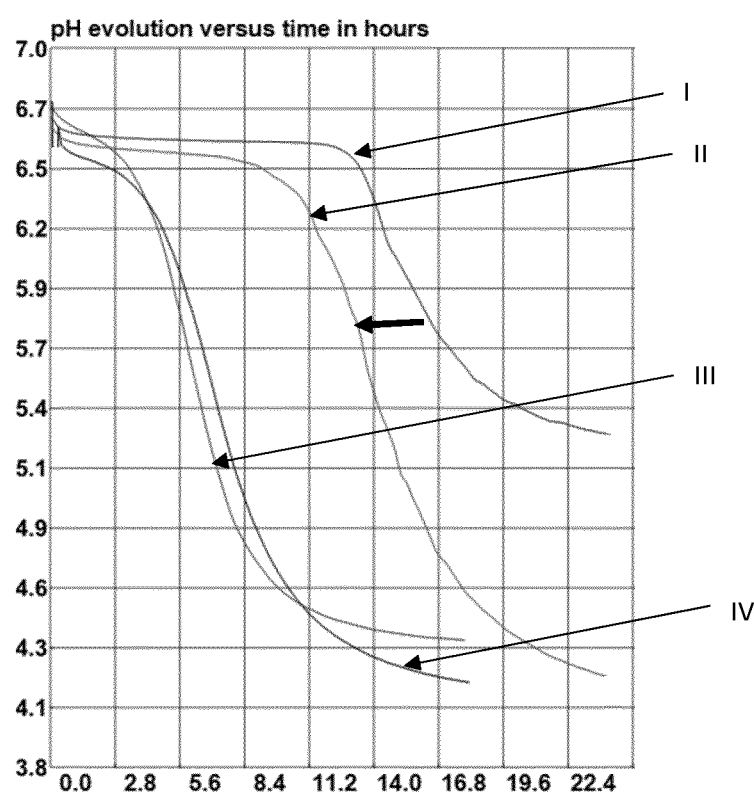
FIG. 15: pH curves monitored by Cinac for one of the preconditioning experiments of *B. longum* strain NCC4020 on BMOS as GOS source: (III) biomass production on dextrose, (IV) biomass production on GOS source, (I) biomass grown on dextrose upon exposure to GOS source, (II) biomass grown on GOS source upon re-exposure to GOS source. Shift in acidification during re-exposure to GOS source is indicated by the bold horizontal arrow.

For *B. longum* strain NCC4020 which possesses the galA gene, a slightly lower final pH was observed for cells propagated on BMOS compared to dextrose (FIG. 15). Upon (re-)exposure of the produced biomass to BMOS, preconditioned cells showed an acidification curve with the same shape but an approximately 6 h longer lag phase compared to the curve measured during growth of biomass on BMOS. However, cells that were previously grown on dextrose had an even longer lag phase and discontinued acidification at a pH of 5.3. This observation corresponded with the low cell counts measured for this fermentation.

In summary, there were no losses observed due to exposure to gastric juice for any of the strains. Furthermore, a preconditioning effect, characterized by a shorter lag phase for biomass previously grown on BMOS, was observed for all strains.

EXAMPLE 2

Preconditioning of *Bifidobacterium Animalis* ssp. *Lactis* with Various GOS Concentrations A preconditioning experiment was performed by growing *Bifidobacterium lactis* NCC2818 on BMOS and on dextrose as carbon source, as described in Example 1, section 3, but varying the concentration of BMOS and of dextrose in the fermentation medium. BMOS was used in concentrations such as to provide 0.28, 0.48, 0.95. 1.44. 1.92, 2.4 and 2.88% of GOS. BMOS having a content of GOS of 48%, these concentrations of pure GOS correspond to amounts of BMOS of 0.6, 1, 2, 3, 4, 5 and 6%, respectively.

The *B. animalis* ssp. *lactis* strains were grown in triplicate in 50 mL growth medium (IM+dextrose (30 g/L dextrose, Table 4), IM+BMOS) filled in sterile 100 mL bottles. Media were inoculated with $10^7$ (afu/mL) and incubated at 37° C. in a water bath. Cinac pH monitoring system (Ysebaert, Frepillon, France) was used for monitoring acidification during fermentation, which can be used as an indication for the growth of lactic acid producing bacteria (Spinnler and Corrieu 1989). After fermentation cell counts were determined by flow cytometry and pour plating.

A volume containing $5 \times 10^9$ cells (determined by flow cytometry) was removed from each bottle after fermentation and transferred to sterile Eppendorf tubes. These samples were then centrifuged with a Biofuge pico (Heraeus Instruments, Hanau, Germany) at 16060×g for 5 min. Subsequently, supernatants were discarded and the pellets were resuspended in 1 mL 0.9% NaCl (Sigma, S9888) solution. This washing step was repeated another time to remove residues of the growth medium. Of the thereby obtained biomass suspension at $5 \times 10^9$ (afu/mL), 200 μL were added to 1.8 mL gastric juice in a 2 mL Eppendorf tube. Gastric juice contained per liter distilled water 2.3 g pepsin (Sigma, P7000) and 5 g NaCl (Sigma, S9888). It was adjusted to a pH of 4.5 to simulate infant conditions. Tubes with the biomass—gastric juice mixture were vortexed well and subsequently incubated in a water bath at 37° C. for 30 min. 100 µL of sample were taken from tubes before and after incubation in order to determine the loss in cell count due to gastric juice by flow cytometry as described in chapter 2.4. The bacterial cells were then re-exposed to BMOS. Of the remaining biomass-gastric juice mixture a volume containing $5 \times 10^8$ cells was used to inoculate 50 mL of IM+BMOS ($10^7$ (afu/mL)). Subsequent incubation, pH monitoring by Cinac and determination of cell count after fermentation were performed the same way as previously described. For each condition tested, the amount of bacteria used to inoculate for the preconditioning and the (re-) exposure steps, the concentration of BMOS for the (re-) exposure step, the gastric juice step, the media and the temperature were always the same. The only difference between the different tested conditions was the carbon source (either BMOS or dextrose) and the concentration of the carbon source used during the preconditioning step. To compare the different conditions, the time to obtain the maximum acidification rate (TM), meaning the inflection point of the pH curves obtained through the Cinac monitoring system, was used as it is an objective parameter to assess how fast bacteria grow. A low TM means a fast bacterial growth.

Figure 16:
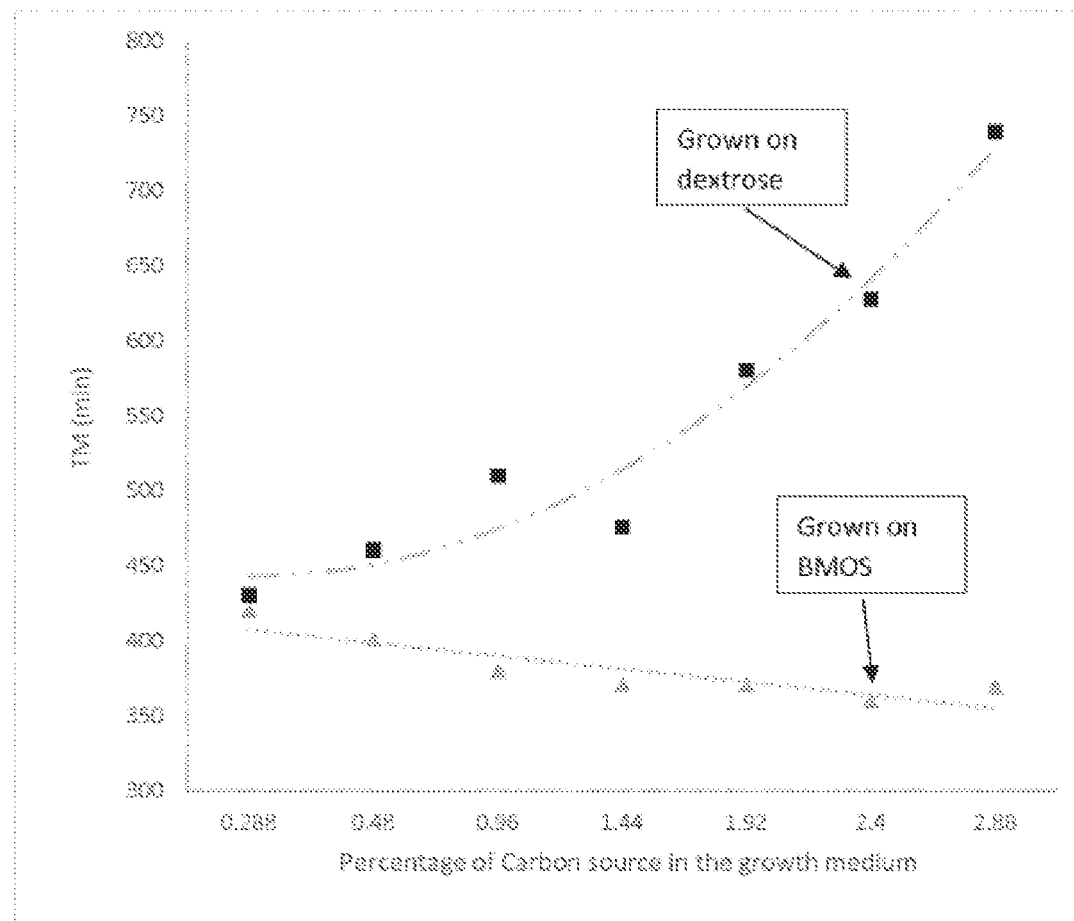
FIG. 16: Cell growth speed of *B. animalis* ssp. *lactis* strain NCC 2818 previously grown with different percentage of BMOS (triangles) or dextrose (squares) as the carbon source, upon (re-)exposure to BMOS.

As shown in FIG. 16, the growth of *B. animalis* ssp. *lactis* upon re-exposure to BMOS, was faster for the bacteria previously grown on BMOS than for the bacteria previously grown on dextrose, indicating that the preconditioning effect is achieved in a wide range of concentrations and even at concentrations as low as 0.28%.

EXAMPLE 3

Effect of Preconditioned *B. Animalis* ssp. *Lactis* on Infant Microbiota

The aim of this experiment was to evaluate the pro- and synbiotic effect of different formulations (preconditioned or non preconditioned probiotic bacteria with or without GOS) versus a negative control during short-term colonic incubations (48 h). The goal of these colonic incubations was to assess the effects of administration of the blank, of the probiotic bacteria alone and of the probiotic bacteria with GOS on the microbial activity (total short chain fatty acids (SOFA), acetate, lactate and ammonium production) of a real infant microbiota and to assess if the effect was different when the probiotic bacteria was preconditioned (i.e. was produced by fermentation with GOS as carbon source. In order to do so, the test ingredients were added to a reactor in which the proximal colon environment of babies was simulated. To select an appropriate donor for the experiment, five 3-month old babies were screened prior to the experiment.

1. In-Vitro Modeling of the Gastrointestinal Tract

In these experiments, a simplified simulation of the continuous Simulator of the Human Microbial Ecosystem (SHIME®) was used. This SHIME® model has been extensively used for more than 20 years for both scientific and industrial projects and has been validated with in vivo parameters. Upon stabilization of the microbial community in the different regions of the colon, a representative microbial community is established in the three colon compartments, which differs both in composition and in functionality in the different colon regions. A single stage batch system mimicking the colonic conditions was used in these experiments as simplified SHIME® system.

2. Short-Term Colonic Incubations

Fecal material from five 3-month old baby donors was collected and preserved with a cryoprotectant. Upon collection of all fecal samples, a pre-screening experiment was performed to select the most appropriate donor for the final experiment. This pre-screening consisted of a short-term colonic incubation, during which BMOS was added to sugar-depleted nutritional medium containing basal nutrients that are present in the colon (e.g. host-derived glycans such as mucin). For each donor, a blank was included containing only sugar-depleted nutritional medium (without fibers) to assess the background activity of the community. Since this was a screening experiment, incubations were performed in single repetition. This resulted in the experimental setup as presented in Table 8 below.

TABLE 8

Experimental setup of the pre-screening experiment

| Condition | Donor | Treatment/Blank | BMOS |
|---|---|---|---|
| 1 | A | Treatment | 5 g/L |
| 2 | A | Blank | |
| 2 | B | Treatment | 5 g/L |
| 4 | B | Blank | |
| 5 | C | Treatment | 5 g/L |
| 6 | C | Blank | |
| 7 | D | Treatment | 5 g/L |
| 8 | D | Blank | |
| 9 | E | Treatment | 5 g/L |
| 10 | E | Blank | |

The results of the pre-screening experiment allowed to select the most appropriate donor for the final experiment. Donor A, which was characterized by the strongest bifidogenic effect, yielding high acetate and lactate concentrations, was selected as the donor for the final experiment. At the start of these final short-term colonic incubations, all tested ingredients were added to sugar-depleted nutritional medium (as described above) together with the selected frozen human baby inoculum. A blank was also included. To account for biological variability, all tests were performed in triplicate, resulting in 30 independent incubations, as specified in Table 9.

Incubation conditions of the pre-screening experiment and the final experiment considered incubations during 48 h at 37° C., under shaking (90 rpm) and anaerobic conditions. Inclusion of a blank in both experiments allowed to assess the specific effect of test ingredients on the metabolic and community composition profile of the colonic microbiota.

As a remark, 5 g/L is typically used as optimal dose to perform mode-of-action studies during in vitro batch fermentations. Higher doses might result in an overload of the system and too strong accumulation of microbial metabolites, while a dose considerably lower than 5 g/L would make it more difficult to observe clear effects.

TABLE 9

Experimental setup of the final experiment

| Condition | *B. animalis* ssp. *lactis* | Amount of BMOS (g/L) added in colonic incubation | Replicate |
|---|---|---|---|
| 1 | No | / | A |
| 2 | | | B |

TABLE 9-continued

Experimental setup of the final experiment

| Condition | B. animalis ssp. lactis | Amount of BMOS (g/L) added in colonic incubation | Replicate |
|---|---|---|---|
| 3 | | | C |
| 4 | | 5 | A |
| 5 | | | B |
| 6 | | | C |
| 7 | Grown on dextrose | / | A |
| 8 | | | B |
| 9 | | | C |
| 10 | | 5 | A |
| 11 | | | B |
| 12 | | | C |
| 13 | Grown on BMOS (preconditioned) | / | A |
| 14 | | | B |
| 15 | | | C |
| 16 | | 5 | A |
| 17 | | | B |
| 18 | | | C |

3. Endpoints of Short-Term Incubations

The following analyses allowed to compare the kinetics in the production of bacterial metabolites for the different prebiotics.

Short chain fatty acids (SOFA) are an assessment of the microbial carbohydrate metabolism (acetate, propionate and butyrate) or protein metabolism (branched SOFA) and can be compared to typical fermentation patterns for normal GI microbiota. Samples for SOFA analysis were analyzed after 6 h of incubation.

Figure 17:
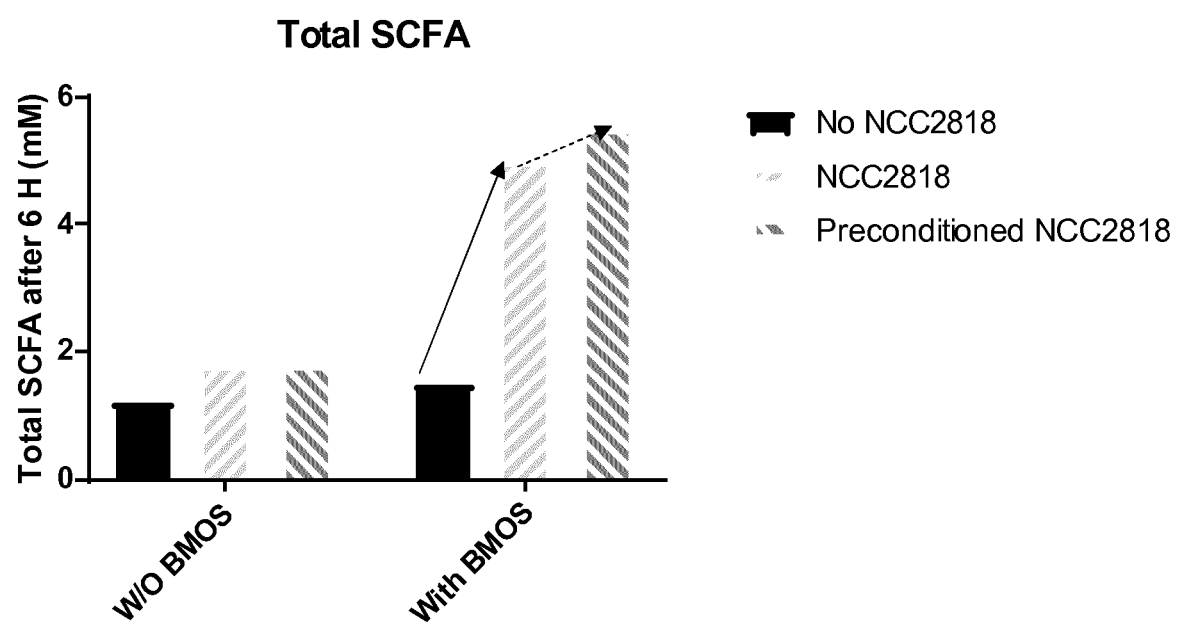
FIG. 17: Total SOFA production after 6 h of fermentation upon administration of 0 g/L or 5 g/L of BMOS as GOS source to the medium or co-supplemented with *B. animalis* ssp. *lactis* strain NCC2818 or preconditioned *B. animalis* ssp. *lactis* strain NCC2818 with the GOS source. Shift in production of total SOFA due to a synergistic effect between *B. animalis* ssp. *lactis* strain NCC2818 and the GOS source is indicated by the bold arrow, whereas the synergistic effect between the preconditioned *B. animalis* ssp. *lactis* strain NCC2818 and the GOS source is indicated by the dotted arrow.
Figure 18:
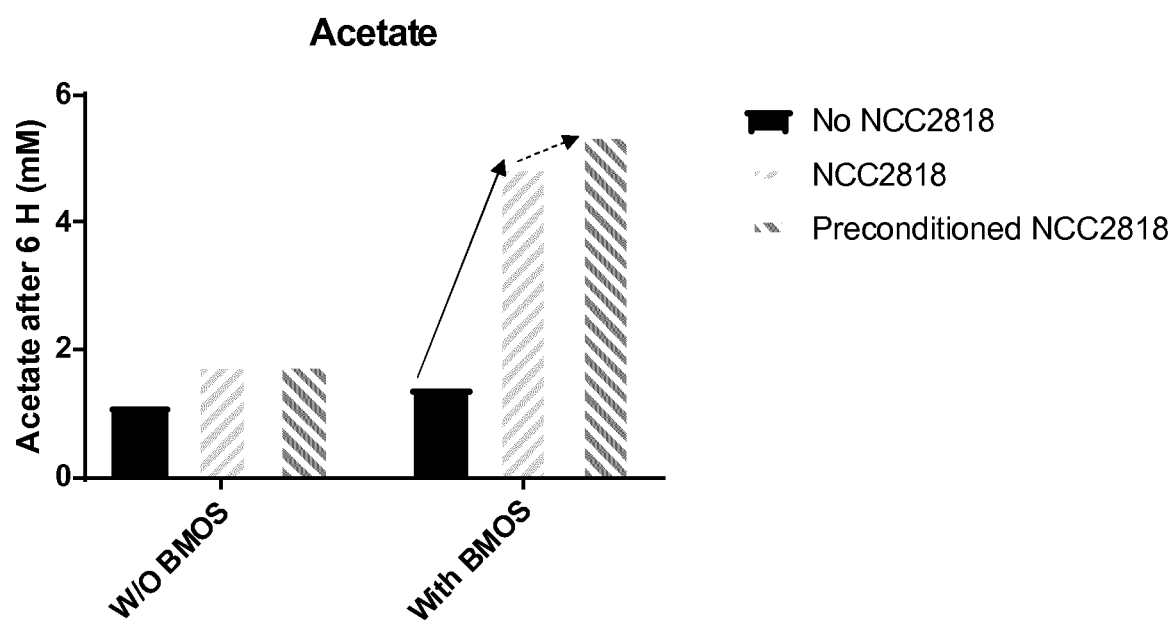
FIG. 18: Acetate production after 6 h of fermentation upon administration of 0 g/L or 5 g/L of BMOS as GOS source to the medium or co-supplemented with *B. animalis* ssp. *lactis* strain NCC2818 or preconditioned *B. animalis* ssp. *lactis* strain NCC2818 with the GOS source. Shift in production of acetate due to a synergistic effect between *B. animalis* ssp. *lactis* strain NCC2818 and the GOS source is indicated by the bold arrow, whereas the synergistic effect between the preconditioned *B. animalis* ssp. *lactis* strain NCC2818 and the GOS source is indicated by the dotted arrow.

The total SOFA levels are reflective of the overall fermentation of test ingredients. Administration of BMOS with the non-preconditioned bacteria (grown on dextrose) enhanced the production of total SOFA after 6 h compared to BMOS alone, corresponding to the known synbiotic effect of GOS and B. animalis ssp. lactis. As shown in FIG. 17, the production of total SOFA was further increased when preconditioned bacteria (grown on BMOS) were administered with BMOS. Thus an increased synbiotic effect is demonstrated. The increase in total SOFA is mainly due to the increase in acetate since similar pattern was observed with the concentration of acetate on FIG. 18.

Figure 19:
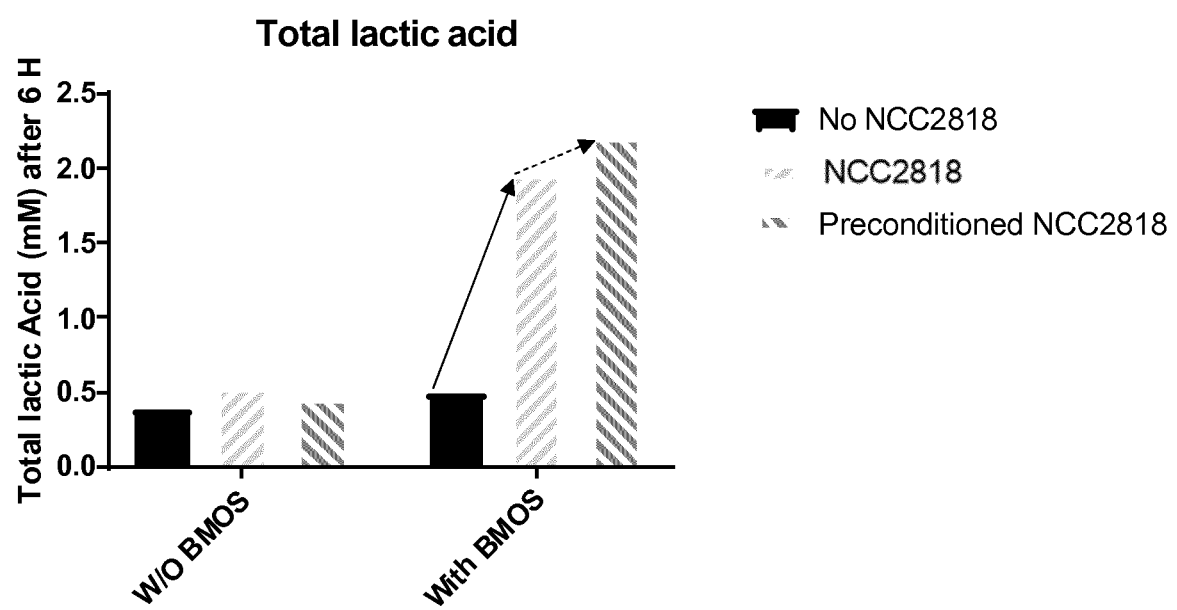
FIG. 19: lactate production after 6 h of fermentation upon administration of 0 g/L or 5 g/L of BMOS as GOS source to the medium or co-supplemented with *B. animalis* ssp. *lactis* strain NCC2818 or preconditioned *B. animalis* ssp. *lactis* strain NCC2818 with the GOS source. Shift in production of lactate due to a synergistic effect between *B. animalis* ssp. *lactis* strain NCC2818 and the GOS source is indicated by the bold arrow, whereas the synergistic effect between the preconditioned *B. animalis* ssp. *lactis* strain NCC2818 and the GOS source is indicated by the dotted arrow.

Lactate analysis: the human intestine harbors both lactate-producing and lactate-utilizing bacteria. Lactate is produced by lactic acid bacteria and decreases the pH of the environment, thereby also acting as an antimicrobial agent. Protonated lactic acid can penetrate the microbial cell after which it dissociates and releases protons within the cell, resulting in acidification and microbial cell death. It can also be rapidly converted into especially butyrate by other microorganisms. Samples for lactate analysis were analyzed after 6 h of incubation. A synbiotic effect is observed when BMOS and B. animalis ssp. lactis grown on dextrose are administered. Such effect is further increased when the administered B. animalis ssp. lactis is preconditioned (grown on BMOS), as shown in FIG. 19.

Figure 20:
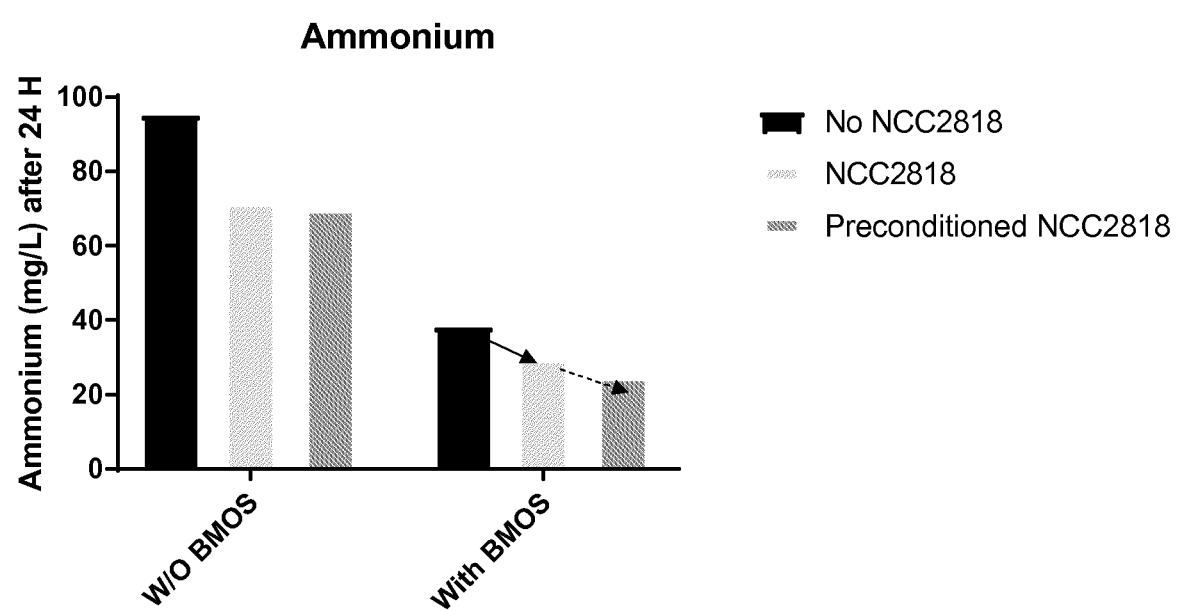
FIG. 20: Ammonium production after 24 h of fermentation upon administration of 0 g/L or 5 g/L of BMOS as GOS source to the medium or co-supplemented with *B. animalis* ssp. *lactis* strain NCC2818 or preconditioned *B. animalis* ssp. *lactis* strain NCC2818 with the GOS source. Shift in production of ammonium due to a synergistic effect between *B. animalis* ssp. *lactis* strain NCC2818 and the GOS source is indicated by the bold arrow, whereas the synergistic effect between the preconditioned *B. animalis* ssp. *lactis* strain NCC2818 and the GOS source is indicated by the dotted arrow.

Ammonium is a product of proteolytic degradation and can also be used as an indirect marker for substrate availability. Samples for ammonium analysis were analyzed 24 h after starting the incubation. FIG. 20 shows that the ammonium production is decreased when the preconditioned B. animalis ssp. lactis is administered, compared to administration of the bacteria grown on dextrose. Ammonium is produced as a result of proteolytic fermentation, associated with the production of toxic compounds such as p-cresol. Therefore, high ammonium levels have been associated with detrimental health effects in the colon. Reduced levels of this metabolite are thus considered beneficial.

This demonstrated increased synbiotic effect obtained due to the fermentation of the probiotic bacteria with a source of GOS as the carbon source translates in various health benefits in the infant, such as a healthier microbiota and associated benefits. The kinetics of the effects observed in a time frame of six hours is also consistent with an infant feeding pattern, as infants are usually fed every three hours in average.

EXAMPLE 4

Preconditioning Effect of Spray-Dried Bifidobacterium Animalis ssp. Lactis NCC2818

The preconditioning experiment of Example 1, Section 3, with the difference that the B. animalis ssp. lactis bacteria were spray-dried after being harvested from the fermentation medium before re-exposure to the source of GOS.

The bacteria were spray-dried as follows: the total solid percentage of the biomass was assessed with a microwave and infrared moisture analyzer (SMART Turbo, CEM Corporation, USA) in order to know the amount of protective agent powder (PA) to weight. The protective agent (which has the composition described in Table 10 below) was then resuspended with sterile water and stirred in a 60° C. bath until complete dissolution, before being mixed with the biomass. The biomass-PA mix was then stirred for 1 H in an ice bucket and the pH adjusted to 7.0 with 30% NaOH before being spray-dried. The spray drying step was performed using a mini spray-dryer B-290 (Buchi, Switzerland) with an inlet temperature below 115° C. and outlet temperature bellow 80° C.

TABLE 10

Composition of the protective agent

| Ingredient | Variant M |
|---|---|
| Maltodextrin DE6 | 52.00 |
| Sodium ascorbate | 23.80 |
| L-Lysine HCL | 10.00 |
| L-Cysteine HCL | 4.20 |
| L-Alanine | 10.00 |
| Total | 100.00 |

Before re-exposure to BMOS, the bacteria were rehydrated at 1:100 in a 0.9% NaCl solution. The cell count was determined by flow cytometry as described in Example 1, section 2.4, and a volume containing $5 \times 10^8$ cells was used to inoculate 50 mL of IM+BMOS ($10^7$ (afu/mL)). Subsequent incubation, pH monitoring by Cinac and determination of cell count after fermentation were performed.

Figure 21:
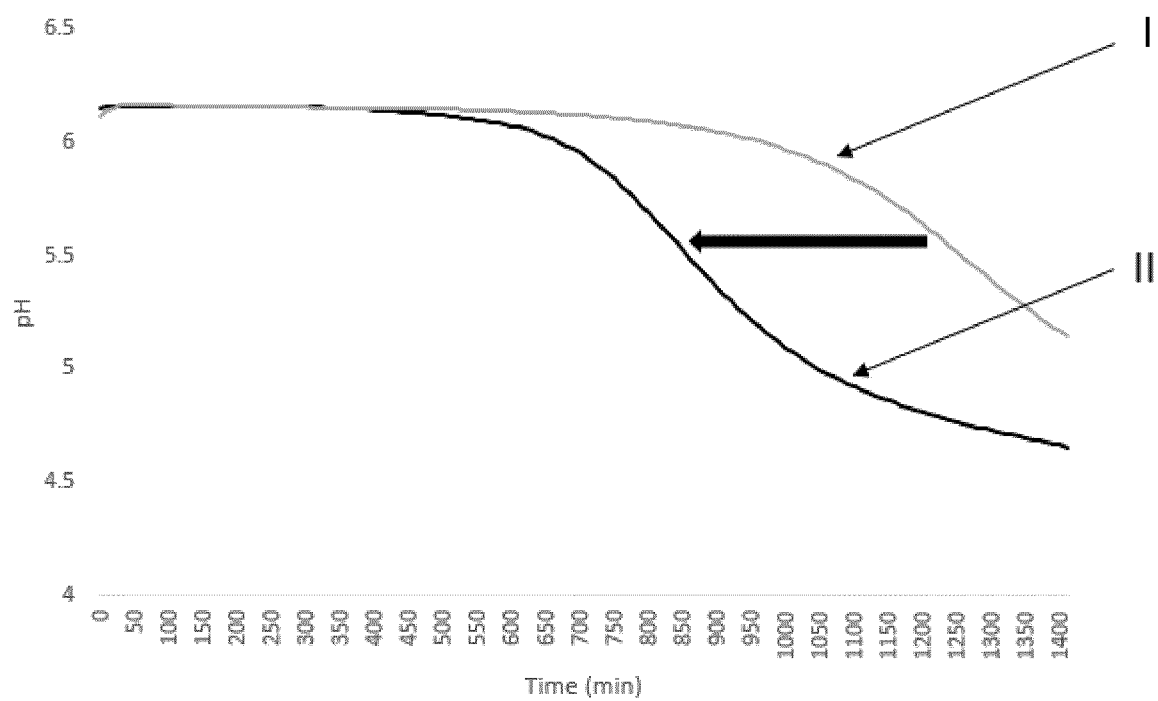
FIG. 21: pH curves monitored by iCinac for one of the preconditioning experiments of spray dried *B. animalis* ssp. *lactis* strain NCC2818 on BMOS as GOS source. (I) Biomass grown on dextrose upon exposure to GOS source, (II) biomass grown on GOS source upon re-exposure to GOS source. Shift in acidification during re-exposure to GOS source is indicated by the bold horizontal arrow.

As shown on FIG. 21, the lag phase was significantly reduced for the preconditioned bacteria compared to the bacteria grown on dextrose. These results demonstrate that a bacteria subjected to a drying step retains its advantageous effects.

EXAMPLE 5

Preconditioning of Selected Lactobacillus Strains

The preconditioning experiment described in Example 1, Section 3, was repeated with Lactobacillus johnsonii NCC533 (deposited as CNCM I-1225) and with BMOS as source of GOS.

L. johnsonii NCC533 has been selected in this experiment as it comprises the full galCDEGR(A) operon, excluding galA.

Figure 22:
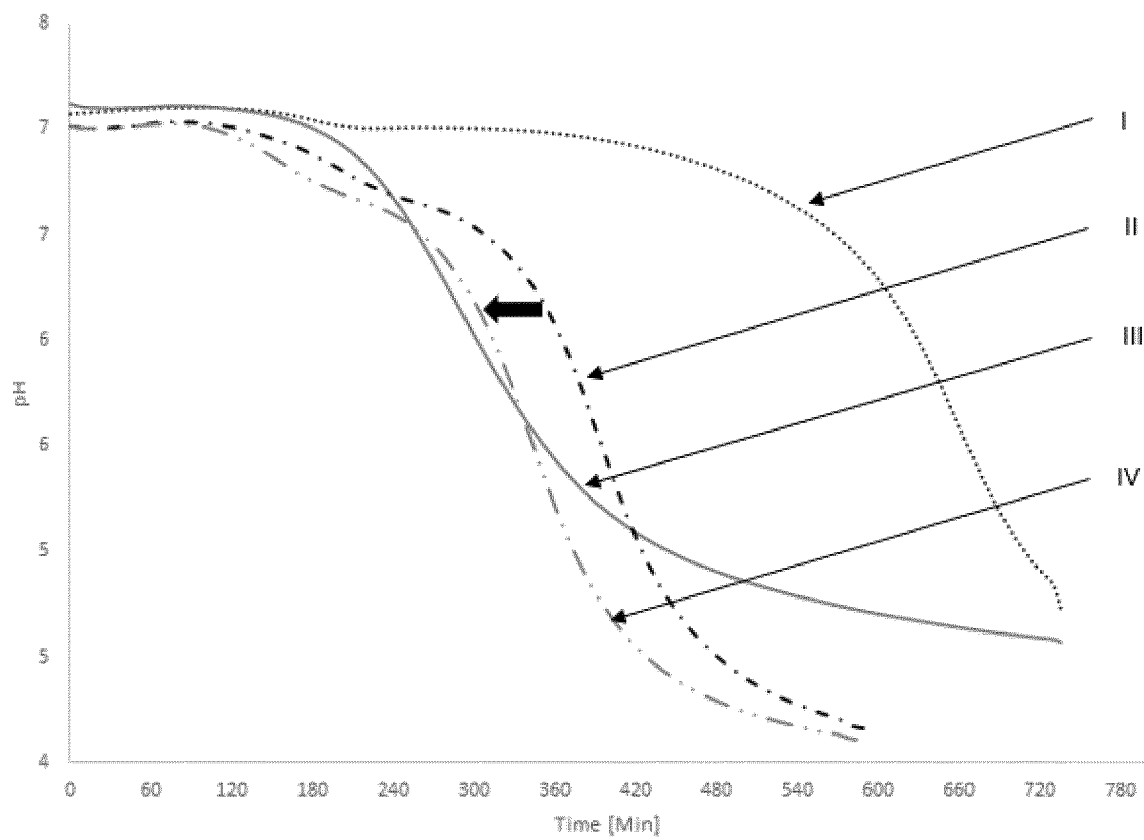
FIG. 22: pH curves monitored by iCinac for one of the preconditioning experiments of *Lactobacillus johnsonii* strain NCC533 on BMOS as GOS source. (I) biomass production on GOS source, (III) biomass production on dextrose, (II) biomass grown on dextrose upon exposure to GOS source, (IV) biomass grown on GOS source upon re-exposure to GOS source. Shift in acidification during re-exposure to GOS source is indicated by the bold horizontal arrow.

The results are provided in FIG. 22. Initial propagation on BMOS and on dextrose are represented with curves I and III, respectively. Although the initial propagation on BMOS started more slowly, suitable growth was obtained at 720 minutes, similar to that obtained when dextrose was used as a carbon source. Curves 11 and IV show the growth curve upon re-exposure to BMOS. As demonstrated previously for the *Bifidobacterium* strains in Example 1, the lag phase of the preconditioned bacteria is significantly shorter than that of the bacteria propagated on dextrose. These results confirm that the beneficial effect of preconditioning of probiotic bacteria is not genus specific, provided that the galCEDEGR (A) operon in present in the bacterial genome.

Figure 23:
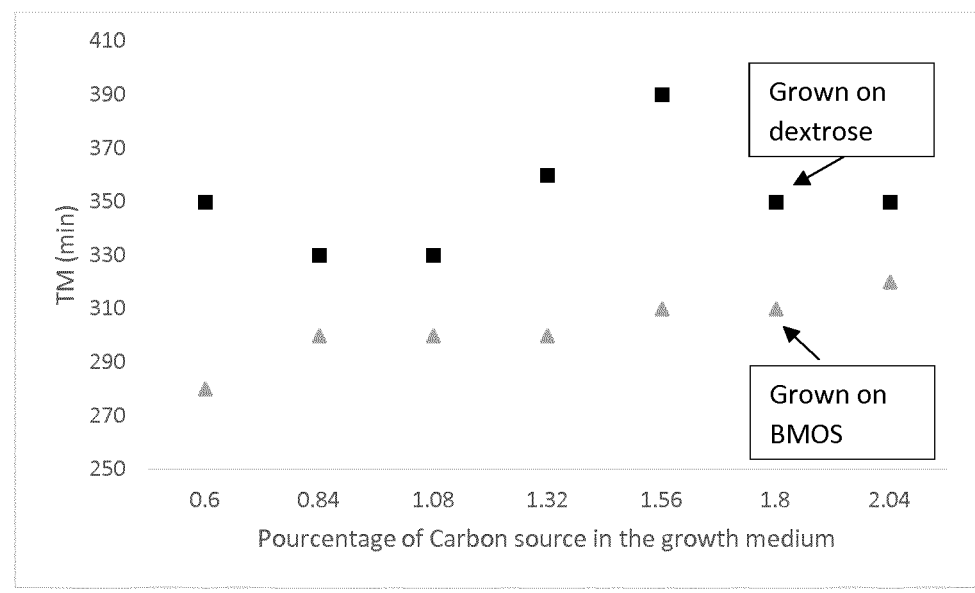
FIG. 23: Cell growth speed of *Lactobacillus johnsonii* strain NCC 533 previously grown with different percentage of BMOS (triangle) or dextrose (square) as the carbon source, upon (re-)exposure to BMOS.

The experiment of Example 2 was also repeated with *L. johnsonii* NCC533, with concentrations of 0.6 to 2.04% of GOS as source of GOS. BMOS being used as carbon source and having a GOS content of 48%, these concentrations correspond to amount of BMOS of 1.25, 1.75, 2.25, 2.75, 3.25, 3.75 and 4.25%, respectively. As shown in FIG. 23, the growth of *L. johnsonii* NCC533 upon re-exposure to BMOS, was faster for the bacteria previously grown on BMOS than for the bacteria previously grown on dextrose, indicating that the preconditioning effect is achieved in a wide range of concentrations.

The invention claimed is:

1. A composition comprising an effective amount of galactooligosaccharides and a probiotic bacteria comprising the galCDEGR(A) operon, wherein the probiotic bacteria is obtained by a process comprising
    fermenting the probiotic bacteria in a bacterial growth medium comprising galacto-oligosaccharides, peptone, and at least one of 3'-sialyllactose or 6'-sialyllactose;
    harvesting the fermented probiotic bacteria, and
    adding additional galacto-oligosaccharides to a culture obtained from the harvesting,
    and the probiotic bacteria comprises *Bifidobacterium*.

2. The composition according to claim 1, wherein the probiotic bacteria is selected from the group consisting of *Bifidobacterium animalis* ssp. *lactis*, *Bifidobacterium longum* and *Bifidobacterium breve*.

3. The composition according to claim 1, wherein the probiotic bacteria is selected from the group consisting of *Bifidobacterium animalis* ssp. *lactis* deposited as CNCM I-3446, *Bifidobacterium longum* deposited as ATCC BAA-999, *Bifidobacterium longum* deposited as ATCC 15707, *Bifidobacterium longum* deposited as CNCM I-5259, and *Bifidobacterium breve* deposited as CNCM I-3914.

4. The composition according to claim 1, wherein the composition comprises at least 0.2% total galacto-oligosaccharides, based on dry matter.

5. The composition according to claim 1, wherein the probiotic bacteria is present in an amount of at least $5 \times 10^5$ cfu/g.

6. The composition according to claim 1, wherein the composition is selected from the group consisting of a food product, a beverage, an animal feed product, a nutritional supplement for human or animal, a pharmaceutical composition, and a cosmetic composition.

7. The composition according to claim 6, which is a nutritional composition selected from the group consisting of infant formula, infant cereals, follow-up formula, growing-up milks, functional milks, and milk products for pregnant and lactating women or for women desiring to get pregnant.

8. A probiotic bacteria comprising the galCDEGR(A) operon, the probiotic bacteria obtained by a process comprising
    fermenting the probiotic bacteria in a bacterial growth medium comprising galacto-oligosaccharides, peptone, and at least one of 3'-sialyllactose or 6'-sialyllactose;
    harvesting the fermented probiotic bacteria, and
    adding additional galacto-oligosaccharides to a culture obtained from the harvesting,
    and the probiotic bacteria comprises *Bifidobacterium*.

9. A process for increasing a therapeutic effect of a composition comprising galactooligosaccharides and a probiotic bacteria comprising the galCDEGR(A) operon, the process comprising:
    fermenting the probiotic bacteria in a bacterial growth medium comprising galacto-oligosaccharides, peptone, and at least one of 3'-sialyllactose or 6'-sialyllactose;
    harvesting the fermented probiotic bacteria, and
    adding additional galacto-oligosaccharides to a culture obtained from the harvesting,
    before incorporating the probiotic bacteria into the composition,
    and the probiotic bacteria comprises *Bifidobacterium*.

10. The process according to claim 9, wherein the therapeutic effect selected from the group consisting of to modulate the immune defenses of a subject, to boost the immune defenses of a subject, to prevent, treat or reduce infections in a subject, to prevent, treat or reduce inflammation in a subject, to prevent allergic reactions in a subject, to promote healthy microbiota in the gastrointestinal tract of a subject, to increase total short chain fatty acid production in the gastrointestinal tract of a subject, to increase acetate production in the gastrointestinal tract of a subject, to increase the production of lactic acid in the gastrointestinal tract of a subject, and to improve the activity of the microbiota in the gastrointestinal tract of a subject.

11. The composition according to claim 1, wherein the probiotic bacteria comprises *Bifidobacterium animalis* ssp. *Lactis*.

12. The probiotic bacteria according to claim 8 comprising *Bifidobacterium animalis* ssp. *Lactis*.

13. The process according to claim 9, wherein the probiotic bacteria comprises *Bifidobacterium animalis* ssp. *Lactis*.

14. The composition according to claim 1, wherein the bacterial growth medium comprises 3'-sialyllactose and 6'-sialyllactose.

15. The composition according to claim 1, wherein the bacterial growth medium further comprises one or more of lactose, glucose, or galactose.

16. The probiotic bacteria according to claim 8, wherein the bacterial growth medium comprises 3'-sialyllactose and 6'-sialyllactose.

17. The probiotic bacteria according to claim 8, wherein the bacterial growth medium further comprises one or more of lactose, glucose, or galactose.

18. The process according to claim 9, wherein the bacterial growth medium comprises 3'-sialyllactose and 6'-sialyllactose.

19. The process according to claim 9, wherein the bacterial growth medium further comprises one or more of lactose, glucose, or galactose.

20. The process according to claim 9, wherein the probiotic bacteria comprises *Bifidobacterium animalis* ssp. *Lactis* deposited as CNCM I-3446.

* * * * *